US012678538B2

(12) United States Patent      (10) Patent No.:    US 12,678,538 B2

Zayed et al.      (45) Date of Patent:      Jul. 14, 2026

(54) CELL-EMBEDDED VASCULAR GRAFT FOR TRANSPLANTATION

(71) Applicant: Washington University, St. Louis, MO (US)

(72) Inventors: Mohamed A. Zayed, St. Louis, MO (US); Jeffrey R. Millman, St. Louis, MO (US)

(73) Assignee: Washington University, St. Louis, MO (US)

( * ) Notice: Subject to any disclaimer, the term of this patent is extended or adjusted under 35 U.S.C. 154(b) by 976 days.

(21) Appl. No.: 17/263,379

(22) PCT Filed: Jul. 29, 2019

(86) PCT No.: PCT/US2019/043904

§ 371 (c)(1),
(2) Date: Jan. 26, 2021

(87) PCT Pub. No.: WO2020/023957

PCT Pub. Date: Jan. 30, 2020

(65) Prior Publication Data

US 2021/0290821 A1      Sep. 23, 2021

Related U.S. Application Data

(60) Provisional application No. 62/703,936, filed on Jul. 27, 2018.

(51) Int. Cl.
A61F 2/04      (2013.01)
A61K 38/28      (2006.01)
(Continued)

(52) U.S. Cl.
CPC ............. A61L 27/28 (2013.01); A61K 38/28 (2013.01); A61L 27/16 (2013.01); A61L 27/34 (2013.01);
(Continued)

(58) Field of Classification Search
CPC .......... A61L 27/28; A61L 27/16; A61L 27/34; A61L 27/3834; A61L 27/54; A61L 27/56;
(Continued)

(56) References Cited

U.S. PATENT DOCUMENTS 5,643,712 A * 7/1997 Brasile .................. A61L 27/507
                                                        600/36
5,747,325 A      5/1998 Newgard
(Continued)

FOREIGN PATENT DOCUMENTS

WO      WO-9305730 A1 * 4/1993      ........... A61L 27/507

OTHER PUBLICATIONS

Sullivan, Biohybrid Artificial Pancreas: Long Term Implantation Studies in Diabetic, Pancreatectomized Dogs, Science, May 3, 1991, pp. 718-721, vol. 252, No. 5006, American Association for the Advancement of Science.

(Continued)

*Primary Examiner* — Adam Marcetich

(57)      ABSTRACT

Disclosed herein is a transplantation graft for transplanting cells into a patient. In an aspect, the graft may include a first graft layer having a generally cylindrical configuration defining a lumen therethrough, a coating layer surrounding the first graft layer, and a plurality of cells or vectors implanted in either the first graft layer or the coating layer. Further disclosed herein is a method for transplanting cells into a patient and a method of treating a patient in need thereof. The transplantation graft may be implanted in the patient in an arteriovenous configuration and the coating layer protects the implanted cells from the patient's immune system. The plurality of cells in the transplantation graft may release a biologically active agent in response to a biological factor in blood flowing through the lumen of the transplantation graft.

20 Claims, 24 Drawing Sheets

(51) Int. Cl.

| | |
|---|---|
| *A61L 27/16* | (2006.01) |
| *A61L 27/28* | (2006.01) |
| *A61L 27/34* | (2006.01) |
| *A61L 27/38* | (2006.01) |
| *A61L 27/54* | (2006.01) |
| *A61L 27/56* | (2006.01) |

(52) U.S. Cl.
CPC ........... *A61L 27/3834* (2013.01); *A61L 27/54* (2013.01); *A61L 27/56* (2013.01); *A61L 2300/252* (2013.01); *A61L 2300/43* (2013.01)

(58) Field of Classification Search
CPC ........... A61L 2300/252; A61L 2300/43; A61L 27/507; A61L 2300/64; A61L 27/3804; A61L 27/38; A61K 38/28; A61K 35/39; A61K 9/0024; A61K 35/12; A61K 2035/126; A61K 2035/128; A61F 2/022; A61F 2/06; A61F 2/02; A61F 2210/0004
See application file for complete search history.

(56) References Cited

U.S. PATENT DOCUMENTS

| | | | | |
|---|---|---|---|---|
| 10,561,766 | B2 * | 2/2020 | Antoni | ..................... A61L 29/08 |
| 10,912,865 | B2 * | 2/2021 | Min | ......................... A61L 27/18 |
| 11,684,574 | B2 * | 6/2023 | Fedorchak | ........... C12N 5/0691 |
| | | | | 435/395 |
| 2001/0001817 | A1 * | 5/2001 | Humes | ................ A61M 31/002 |
| | | | | 606/198 |
| 2002/0058983 | A1 * | 5/2002 | Dzau | ...................... C12N 5/069 |
| | | | | 623/1.4 |
| 2003/0082148 | A1 * | 5/2003 | Ludwig | .............. A61K 38/1825 |
| | | | | 435/372 |
| 2004/0086493 | A1 * | 5/2004 | Hubbell | ............... A61K 9/1647 |
| | | | | 514/772.3 |
| 2004/0148015 | A1 * | 7/2004 | Lye | ....................... A61L 31/082 |
| | | | | 623/1.15 |

| | | | | |
|---|---|---|---|---|
| 2005/0019370 | A1 | 1/2005 | Humes | |
| 2006/0275338 | A1 * | 12/2006 | Flugelman | .......... A61L 27/3808 |
| | | | | 514/8.1 |
| 2007/0208420 | A1 | 9/2007 | Ameer | |
| 2008/0274201 | A1 * | 11/2008 | Hubbell | ............. A61K 47/6925 |
| | | | | 522/12 |
| 2009/0105811 | A1 * | 4/2009 | Dinh | ...................... A61F 2/915 |
| | | | | 623/1.41 |
| 2010/0279268 | A1 * | 11/2010 | Neumann | .............. C12M 25/14 |
| | | | | 435/284.1 |
| 2011/0300616 | A1 * | 12/2011 | Neumann | .............. C12M 21/08 |
| | | | | 435/284.1 |
| 2012/0083767 | A1 * | 4/2012 | Gerstenblith | ......... A61L 31/146 |
| | | | | 604/890.1 |
| 2012/0245705 | A1 * | 9/2012 | Hasilo | ................ A61L 27/3834 |
| | | | | 604/93.01 |
| 2013/0023823 | A1 * | 1/2013 | Simpson | .............. A61K 9/5036 |
| | | | | 604/93.01 |
| 2014/0147483 | A1 * | 5/2014 | Hubbell | ............... A61K 9/2027 |
| | | | | 424/423 |
| 2014/0271843 | A1 * | 9/2014 | Ma | ........................ A61K 9/0024 |
| | | | | 424/463 |
| 2014/0309726 | A1 | 10/2014 | Wang | |
| 2015/0023911 | A1 * | 1/2015 | Schilling | ................. A61L 15/44 |
| | | | | 435/375 |
| 2017/0226232 | A1 * | 8/2017 | Vegas | .................. C12N 5/0677 |
| 2017/0239391 | A1 * | 8/2017 | Rotem | .................... A61L 27/56 |
| 2018/0119106 | A1 | 5/2018 | Millman | |
| 2018/0318358 | A1 * | 11/2018 | Bach | ....................... A61K 35/39 |
| 2020/0390938 | A1 * | 12/2020 | Ameer | ................... A61F 2/022 |

OTHER PUBLICATIONS

International Search Report and Written Opinion dated Oct. 16, 2019 in corresponding/related International Application No. PCT/US 19/43904 filed Jul. 29, 2019, 8 pages.
European Search Report dated Mar. 18, 2022 in corresponding/related European Application No. EP 19840605 filed Jul. 29, 2019, 2 pages.

* cited by examiner

PET Glucose 3hr

PET Insulin 3hr

CELL-EMBEDDED VASCULAR GRAFT FOR TRANSPLANTATION

CROSS-REFERENCE TO RELATED APPLICATIONS

This application claims the benefit of International Patent Application No. PCT/US2019/043904 filed Jul. 29, 2019, the contents of which are incorporated by reference in its entirety. International Patent Application No. PCT/US2019/043904 claims priority to U.S. Provisional Application No. 62/703,936 filed Jul. 27, 2018, the contents of which are incorporated by reference in its entirety.

STATEMENT REGARDING FEDERALLY SPONSORED RESEARCH

Not Applicable.

FIELD

The present invention relates to cell-embedded vascular grafts for tissue transplantation.

BACKGROUND

Nearly 10 million Americans have Type 1 diabetes (T1D), and its prevalence is increasing. Diabetes is caused by the destruction or dysfunction of insulin-producing pancreatic β cells. There is currently no cure for T1D, and current diabetes treatments are insufficient in controlling the progressive nature of the disease. Patients could potentially be cured by transplantation of exogenous β cells. Until recently, the only source of exogenous β cells was from cadaveric donors, which are in limited supply and are of variable, often poor, quality. Furthermore, transplantation success has been limited by the oxygen supply in microvasculature, which is essential for β cell graft survival and function.

Artificial organs promise to dramatically change the way we treat diseases. However, challenges remain in this rapidly emerging field of regenerative medicine. A large number of cells (>1 billion) are required to make a clinical impact on the patient. These transplanted cells need a sustainable and constant blood supply to survive and function. Furthermore, the cells have to be protected from attack by the host immune system. A major challenge in the field of regenerative medicine is how to deliver the cells in a way that they survive, function, and are protected from the immune system. To date, the technology to simultaneously circumvent these fundamental challenges has not yet been developed.

Therefore, there is a need for device for delivering transplanted cells by providing access to blood supply and protecting the cells from the immune system to allow the transplanted cells to survive and function in the host.

SUMMARY

The disclosure provides a transplantation graft for transplanting cells into a patient. In an aspect, the graft may include a first graft layer having a generally cylindrical configuration comprising a lumen therethrough, a coating layer surrounding the first graft layer, and a plurality of cells implanted in either the first graft layer or the coating layer. The transplantation graft may be implanted in the patient in an arteriovenous configuration and the coating layer protects the implanted cells from the patient's immune system. In an aspect, the plurality of cells in the transplantation graft release a biologically active agent in response to a biological factor in blood flowing through the lumen of the transplantation graft. The transplantation graft may further include a second graft layer between the first graft layer and the coating layer. The first graft layer and/or the second graft layer may be porous or microporous. The implanted cells may be within the first graft layer, second graft layer, and/or the coating layer. The first graft layer and/or second graft layer may include polytetrafluoroethylene (PTFE), expanded PTFE (ePTFE), stretch PTFE, polyethylene terephthalate (DACRON®), polyurethaneurea, polydimethylsiloxane (PDMS), or combinations thereof. The coating layer may include alginate, triazole-thiomorpholine dioxide alginate, polyethylene glycol (PEG), PTFE, polyglycolic acid (PGA), poly-l-lactic acid (PLLA), polyhydroxyalkanoate, polycaprolactone-copolylactic acid, polylactide-coglycolide (PLGA), PDMS, polycaprolactone, or combinations thereof. In an aspect, the coating layer may include alginate and PEG. The implanted cells may be selected from primary cells, pluripotent stem cells, differentiated stem cells, pancreatic cells, islet cells, β cells, thyroid cells, parathyroid cells, pituitary gland cells, adrenal gland cells, liver cells, genetically engineered cells, and any cell which secretes a biologically active agent.

Further provided herein is a method for transplanting cells or other biological agents into a patient. The method may include implanting a plurality of cells, viral vectors, or bacterial vectors, into a first graft layer or a coating layer of a transplantation graft, and implanting the transplantation graft into the patient in an arteriovenous configuration. In an aspect, the cells may be implanted in the transplantation graft after the transplantation graft has been implanted in the patient.

The disclosure further provides a method of treating a patient in need thereof. The method may include implanting a transplantation graft into the patient in an arteriovenous configuration. The transplantation graft may include a first graft layer having a generally cylindrical configuration comprising a lumen therethrough, a coating layer surrounding the first graft layer, and a plurality of cells. The plurality of cells in the transplantation graft may release a biologically active agent in response to a biological factor in blood flowing through the lumen of the transplantation graft. The implanted cells may be selected from primary cells, pluripotent stem cells, differentiated stem cells, pancreatic cells, islet cells, β cells, thyroid cells, parathyroid cells, pituitary gland cells, adrenal gland cells, liver cells, genetically engineered cells, and any cell which secretes a biologically active agent. In an aspect, the implanted cells may be stem cell derived β cells. The biological factor may be selected from proteins, peptides, carbohydrates, polysaccharides, and any factor within the blood. In an aspect, the biological factor is glucose. The biologically active agent may be selected from proteins, peptides, hormones, enzymes, and proteases. In an aspect, the biologically active agent is insulin. In other aspects, viral or bacterial vectors are implanted in the transplantation graft to secrete a biologically active agent into the patient.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF DRAWINGS

The description will be more fully understood with reference to the following figures and data graphs, which are presented as various embodiments of the disclosure and should not be construed as a complete recitation of the scope of the disclosure, wherein.

Figure 16:
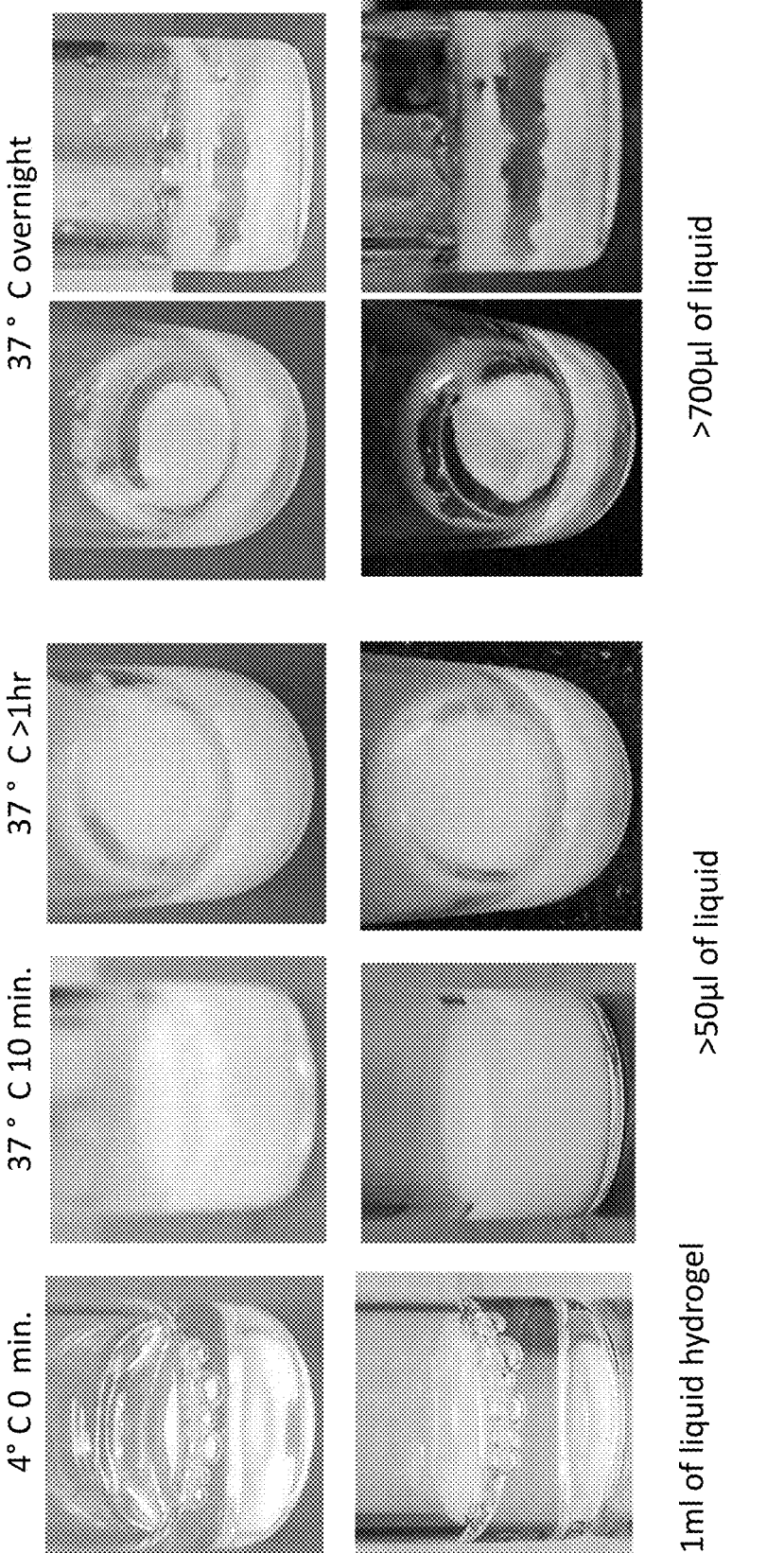
Figure 17A:
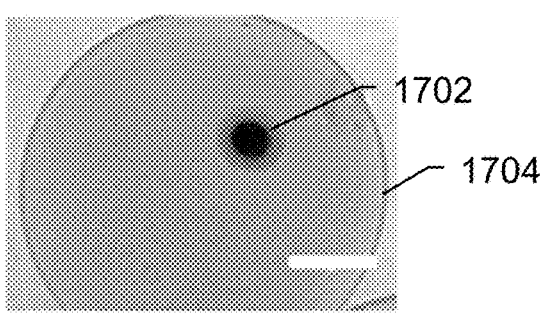
Figure 17B:
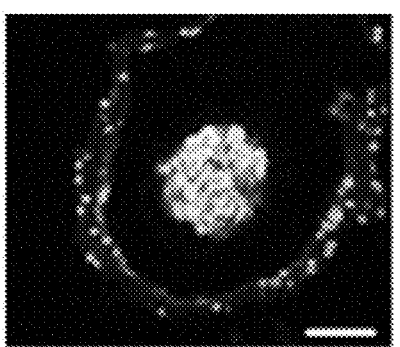
Figure 17C:
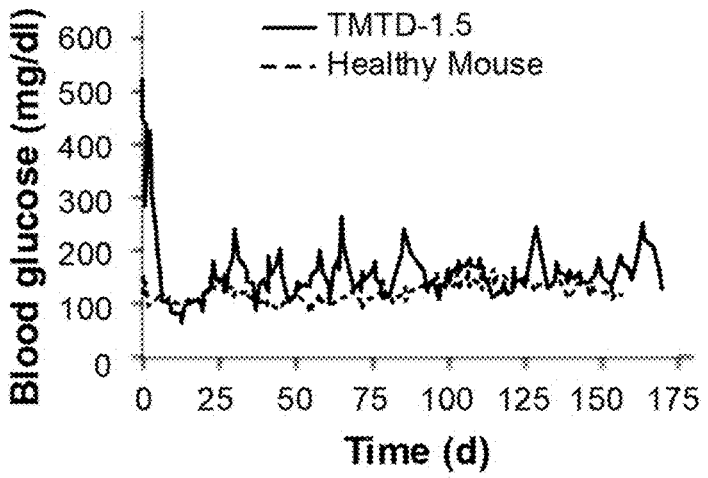
Figure 17D:
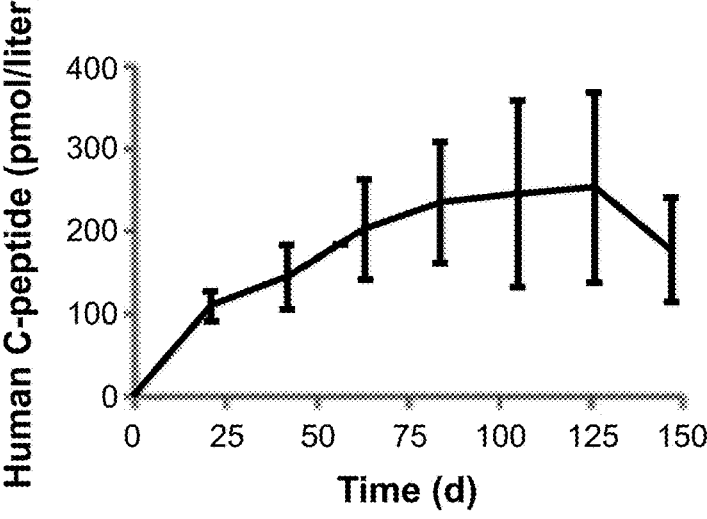
Figure 18:
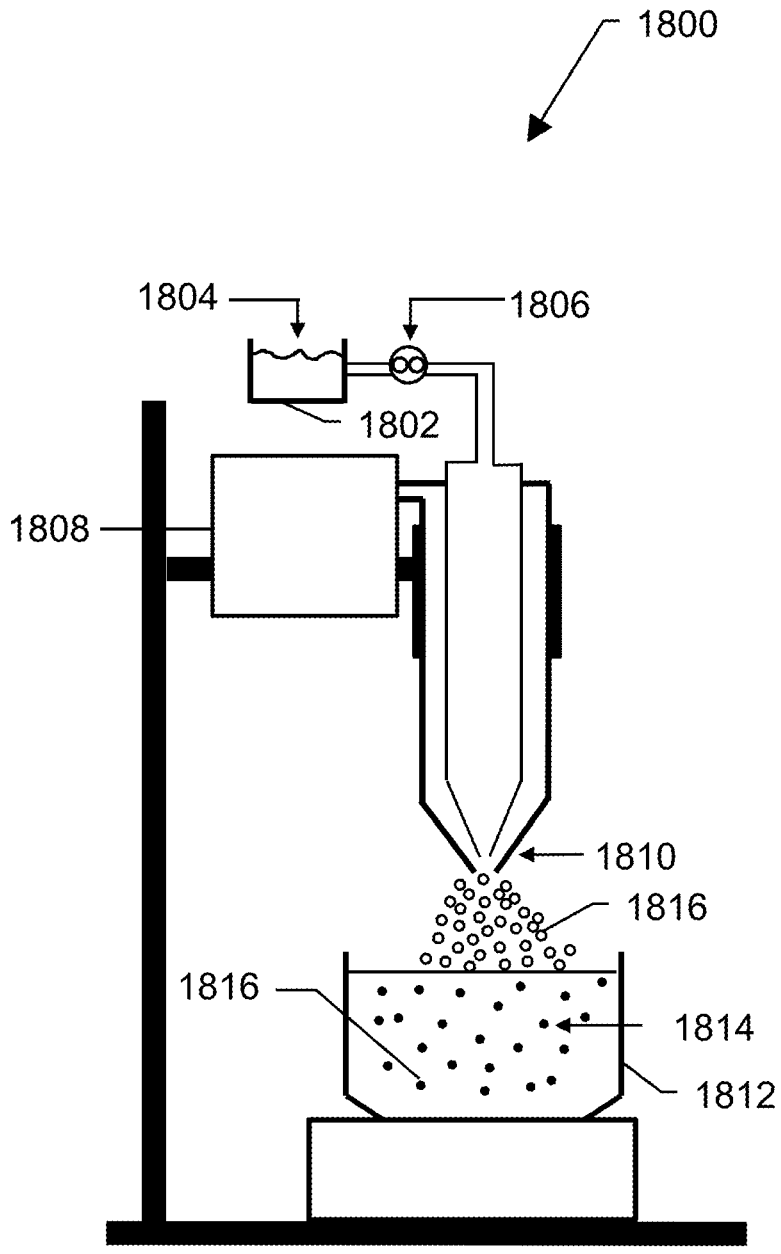
Figure 19:
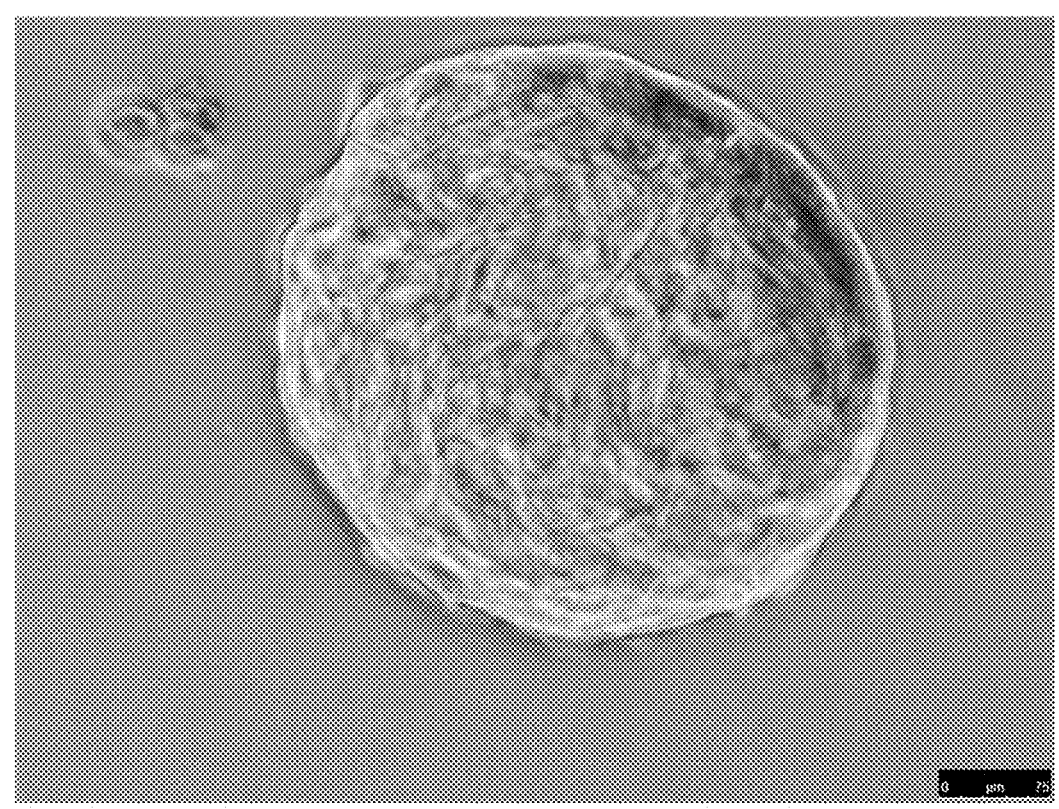
Figure 20:
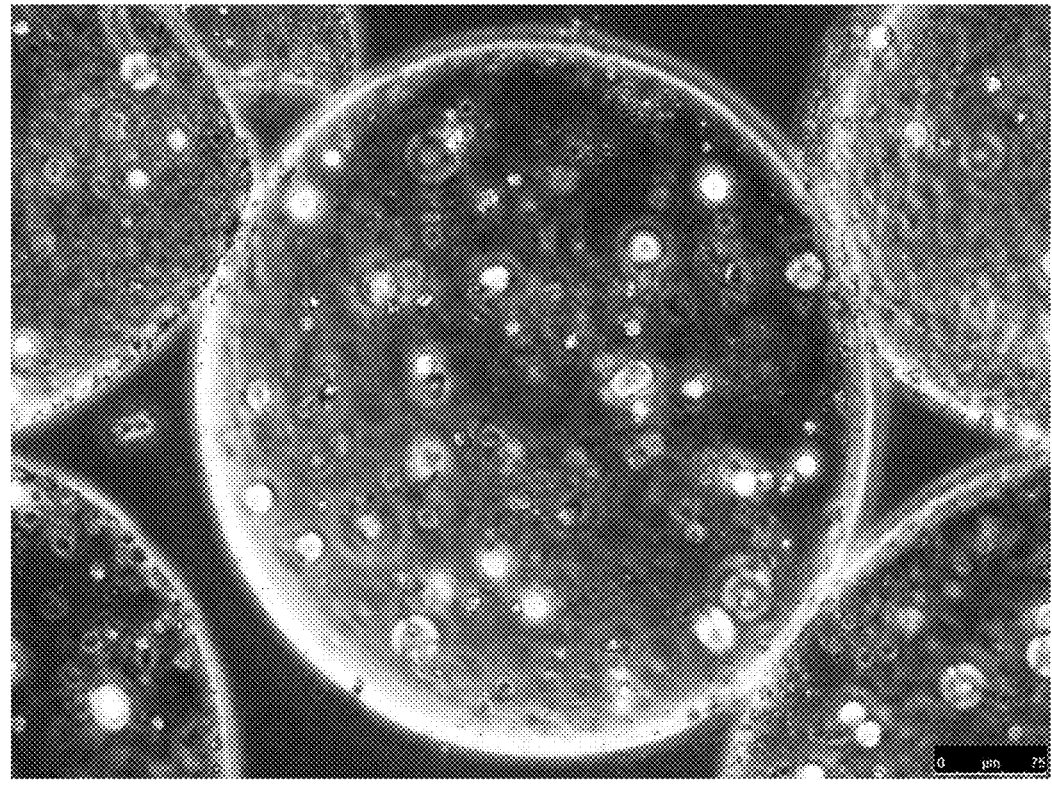
Figure 21A:
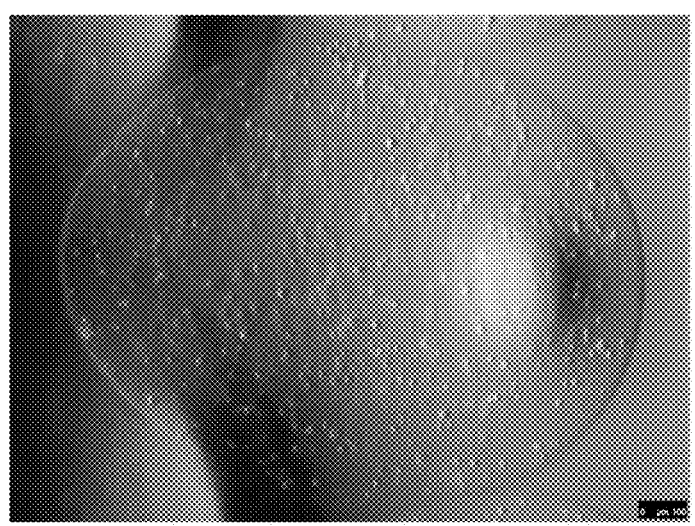
Figure 21B:
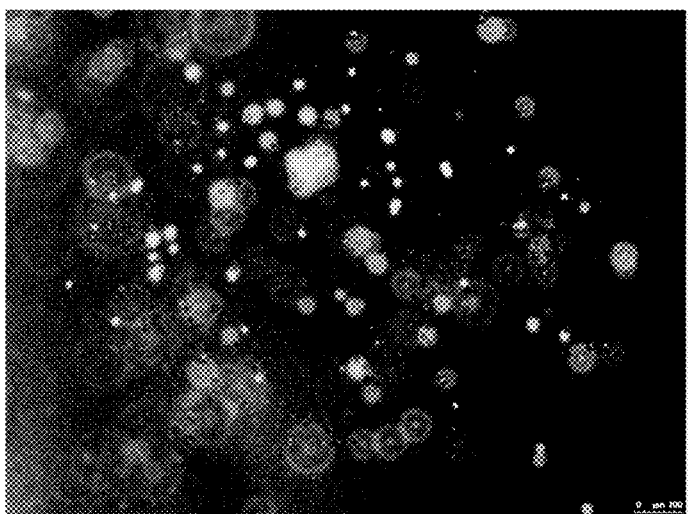
Figure 21C:
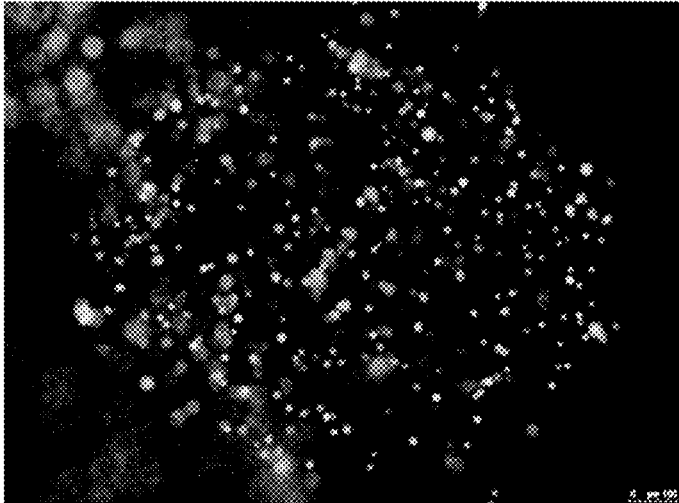
Figure 22A:
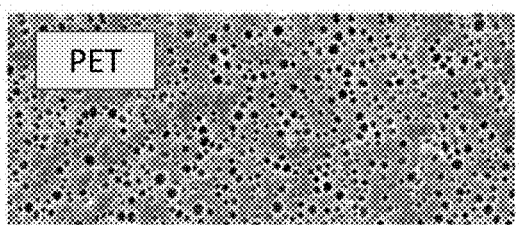
Figure 22B:
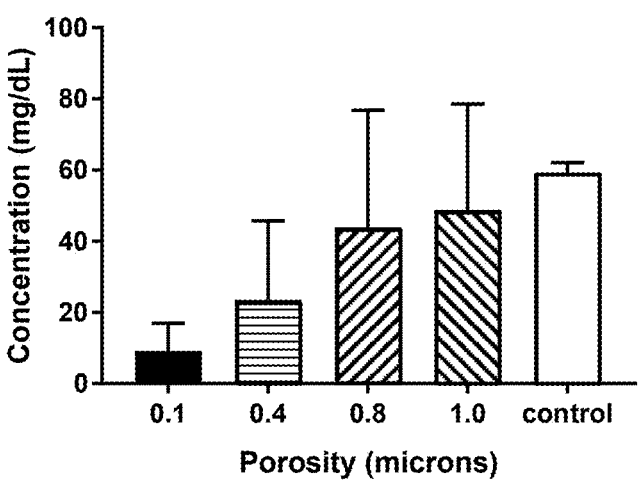
Figure 22C:
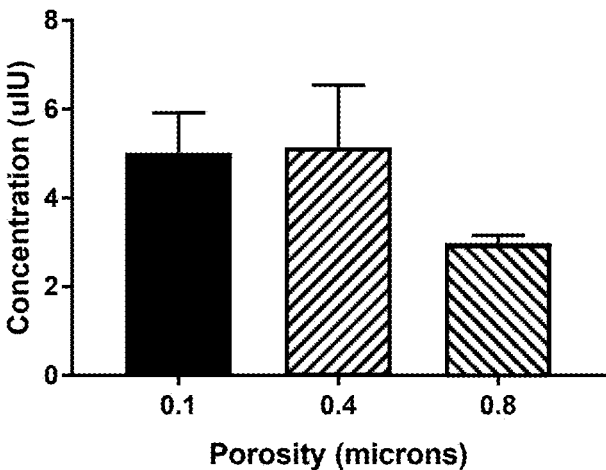
Figure 23A:
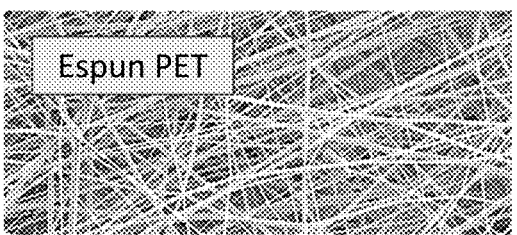
Figure 23B:
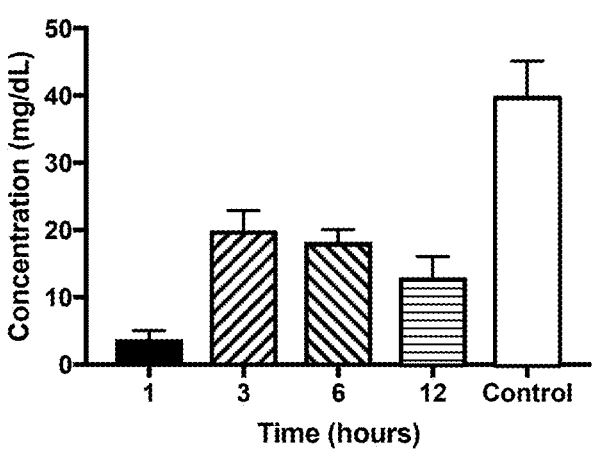
Figure 23C:
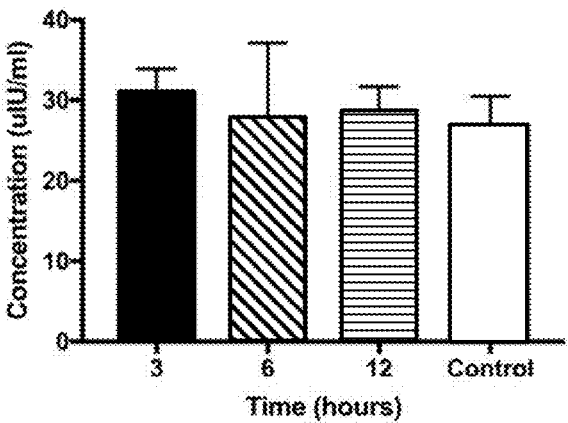
Figure 24A:
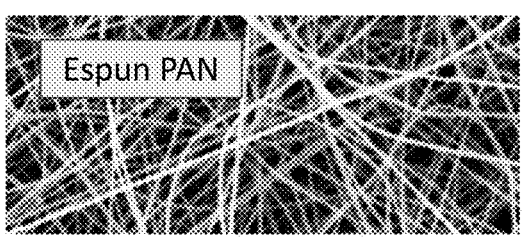
Figure 24B:
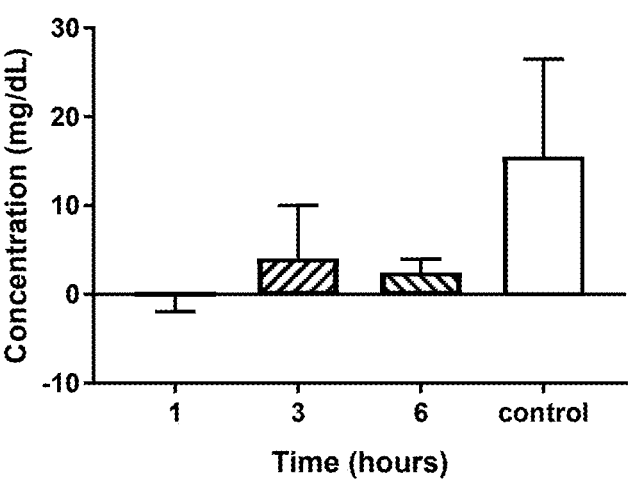
Figure 24C:
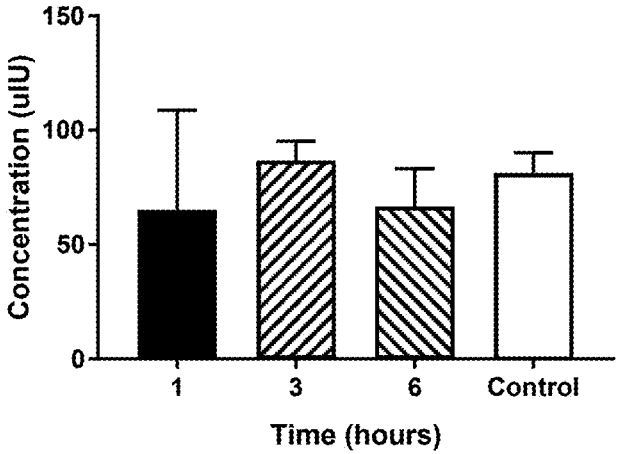
Figure 25:
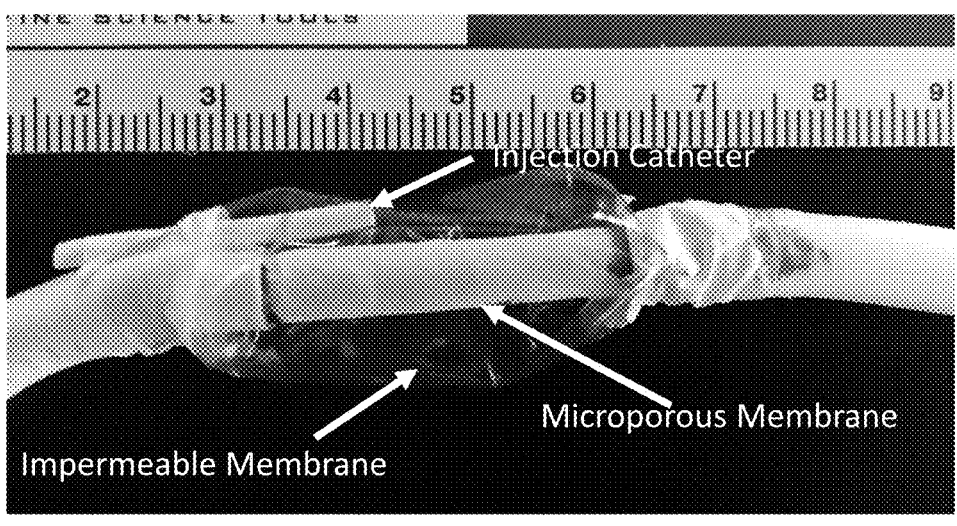
Figure 26:
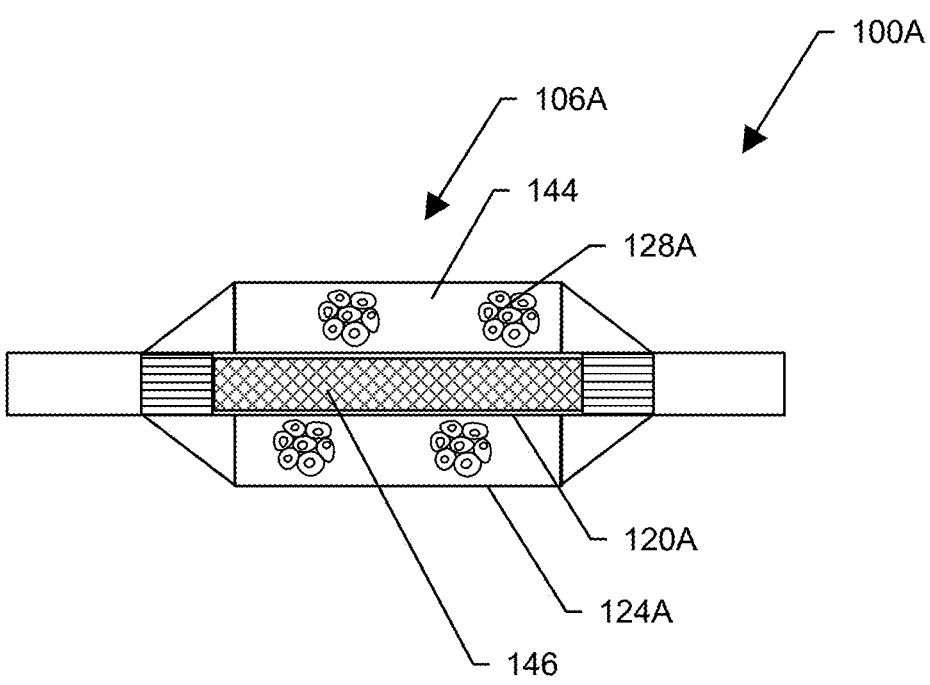
Figure 27:
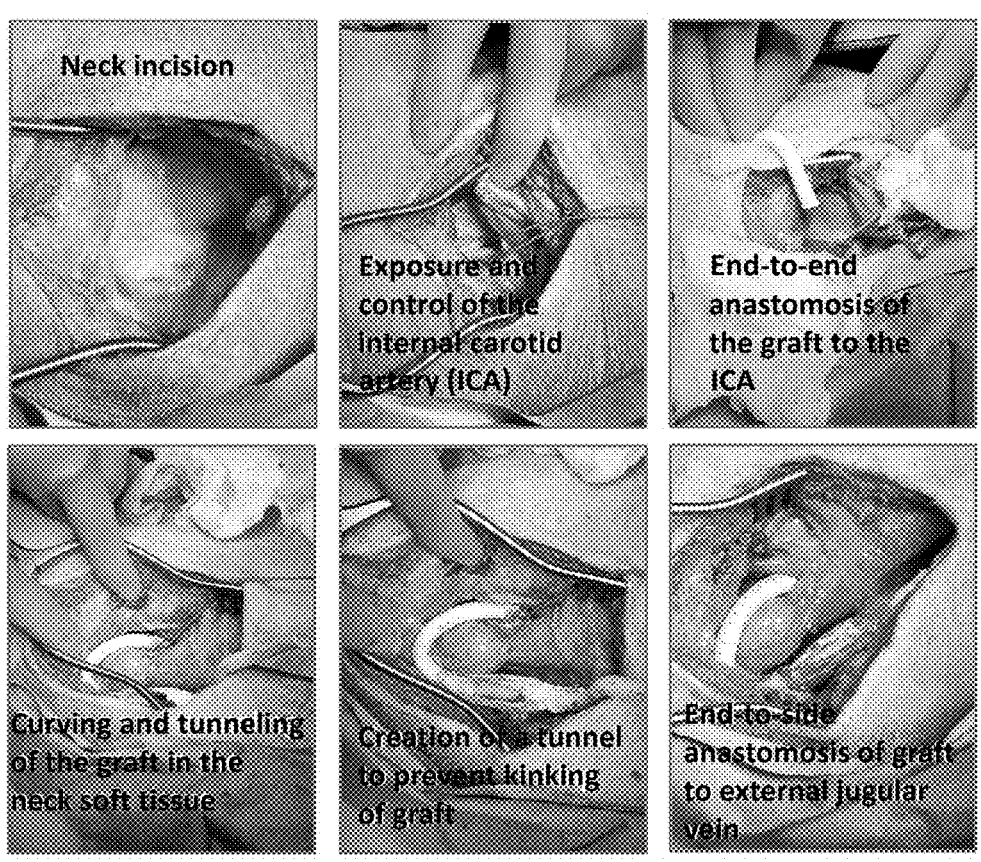
Figure 28:
Figure 29:
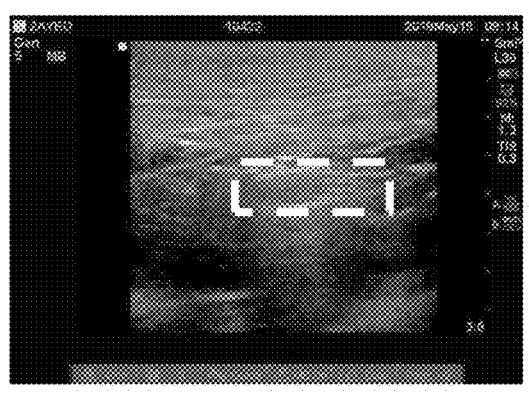
Figure 30:
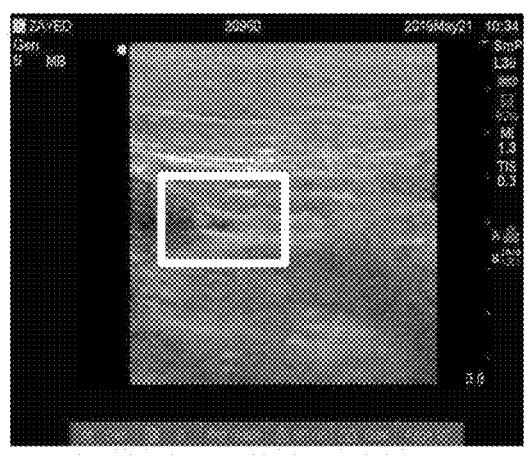
Figure 31:
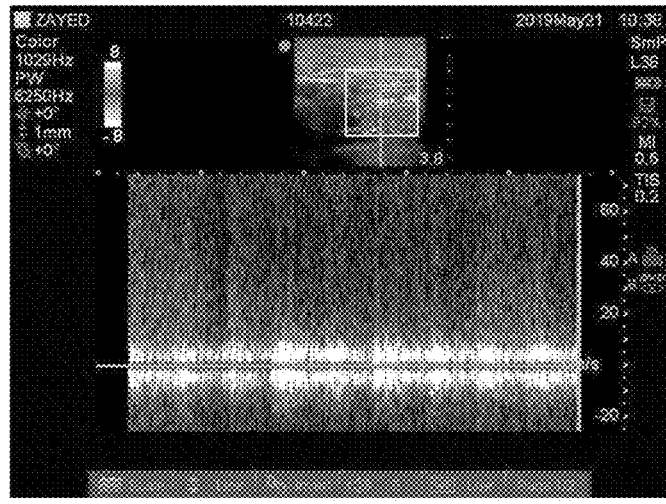
Figure 32:
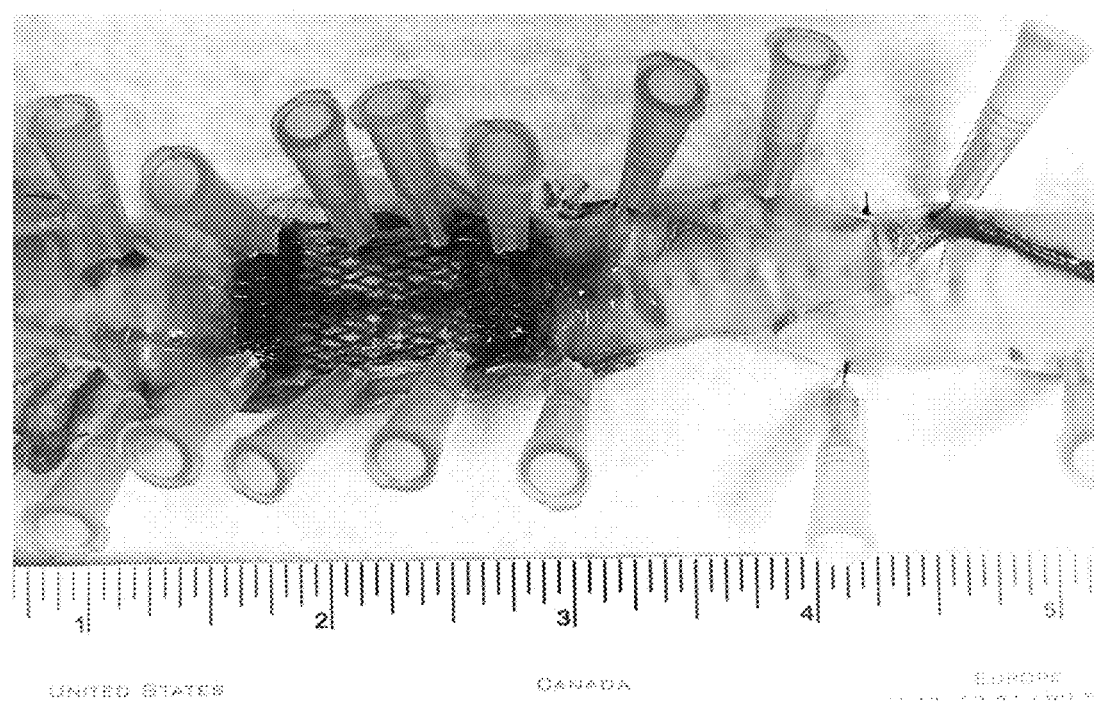

μm PET membrane with a hydrogel outer layer, in which the β-cells are stained to indicate cell activity;

FIG. 16 contains a series of photographs showing mixtures of stem cell-derived β-cells embedded in hydrogels formed at various conditions;

FIG. 17A is a bright field image of a stem cell-derived β-cell cluster imbedded in an alginate microbead;

FIG. 17B is an immunofluorescence image of an alginate microbead with imbedded stem cell-derived β-cell cluster 145 days after implantation in a mouse, stained to indicate insulin production;

FIG. 17C is a graph comparing the blood glucose levels of diabetic mice with implanted stem cell-derived β-cell vs healthy mice;

FIG. 17D is a graph summarizing human C-peptide levels in diabetic mice after transplanting with stem cell-derived β-cells implanted in alginate microbeads;

FIG. 18 is a schematic diagram of a system for making alginate microbeads with embedded cells;

FIG. 19 is a microscopic image of an alginate microbead;

FIG. 20 is a microscopic image of an alginate microbead embedded with endothelial cells;

FIG. 21A is a microscopic image of an alginate microbead embedded with endothelial cells;

FIG. 21B is a confocal immunofluorescent microscopic image of the microbead of FIG. 21A, stained to show dead cells;

FIG. 21C is a confocal immunofluorescent microscopic image of the microbead of FIG. 21A, stained to show live cells;

FIG. 22A is a microscopic image of a porous PET membrane;

FIG. 22B is a graph summarizing the diffusion of glucose through the PET membrane shown in FIG. 22A for various membrane porosities over three hours;

FIG. 22C is a graph summarizing the diffusion of insulin through the PET membrane shown in FIG. 22A for various membrane porosities over three hours;

FIG. 23A is a microscopic image of an electrospun PET membrane;

FIG. 23B is a graph summarizing the diffusion of glucose through the electrospun PET membrane shown in FIG. 23A over 12 hours;

FIG. 23C is a graph summarizing the diffusion of insulin through the electrospun PET membrane shown in FIG. 23A over 12 hours;

FIG. 24A is a microscopic image of an electrospun PAN membrane;

FIG. 24B is a graph summarizing the diffusion of glucose through the electrospun PAN membrane shown in FIG. 24A over 6 hours;

FIG. 24C is a graph summarizing the diffusion of insulin through the electrospun PAN membrane shown in FIG. 23A over 6 hours;

FIG. 25 is a photograph of a transplantation graft in one embodiment;

FIG. 26 is a side view drawing of a transplantation graft in one embodiment;

FIG. 27 is a series of photographs illustrating a surgical procedure to implant a transplantation graft in accordance with one aspect of the disclosure;

FIG. 28 is a photograph of a transplantation graft with cell-embedded alginate particles, corresponding to region within dashed outline in FIG. 28 implanted in a porcine subject;

FIG. 29 is an ultrasound image of the transplantation graft of FIG. 28 (corresponding to region within dashed outline), obtained after completion of implantation procedure;

FIG. 30 is an ultrasound image of the transplantation graft of FIG. 28 (corresponding to an arterial end region within solid rectangle);

FIG. 31 is a graph of flow rate through the transplantation graft of FIG. 28 obtained using Doppler ultrasound; and FIG. 32 is an image of the transplantation graft of FIG. 28 dissected from the porcine subject 3-4 weeks after the initial transplantation.

DETAILED DESCRIPTION

The disclosure may be understood by reference to the following detailed description, taken in conjunction with the drawings as described below. It is noted that, for purposes of illustrative clarity, certain elements in various drawings may not be drawn to scale.

Provided herein is a multi-layered, micro-porous, arteriovenous graft that includes cells for transplantation in various aspects. In some aspects, the cells are organ-specific differentiated stem cells. In one aspect, a large number of biologically active, organ specific (e.g. pancreas, thyroid, adrenal gland) differentiated stem cells are implanted into the graft. In another aspect, the graft is implanted in the peripheral circulatory system of a patient. In this aspect, the graft provides the implanted cells with direct access to arterial blood supply and protection from the host immune system.

Without being limited to any particular theory, proximity to arterial blood may provide enhanced oxygenation to the implanted cells in the arteriovenous graft, rapid sensing of a biological factor such as glucose, and delivery, secretion, and/or consumption of a biologically active agent, such as the delivery of 0 to the blood. This ability to sense and react to biological factors may enhance transplant cell survival and function. In various other aspects, the implanted cells within the graft are protected from the immune system by being embedded into the graft and surrounded by a hydrogel and/or the graft material itself. In various aspects, high oxygenation combined with immune shielding maximizes the survival and function of transplanted SC-β cells, as well as facilitates rapid sensing of arterial blood glucose to prevent clinically detrimental hypoglycemic and hyperglycemic events. In various other aspects, the transplantation graft informs the development of whole artificial organs and enables development of an assembly of complex tissues and microcirculation to recapitulate organ function.

Transplantation Graft

In various aspects, a transplant graft is provided that includes multiple layers configured to enable a plurality of cells to be transplanted into a patient such that the cells are in contact with arterial blood while protecting the cells against immunological reactions from the patient. A transplantation graft 100 is illustrated in one aspect in FIG. 1. In this aspect, the transplantation graft 100 includes a first end 102, a second end 104, and a treatment zone 106 positioned between the first end 102 and the second end 104. In one aspect, the first end 102 and the second end 104 are each tubular and configured to be surgically attached to an artery and/or vein.

Figure 1:
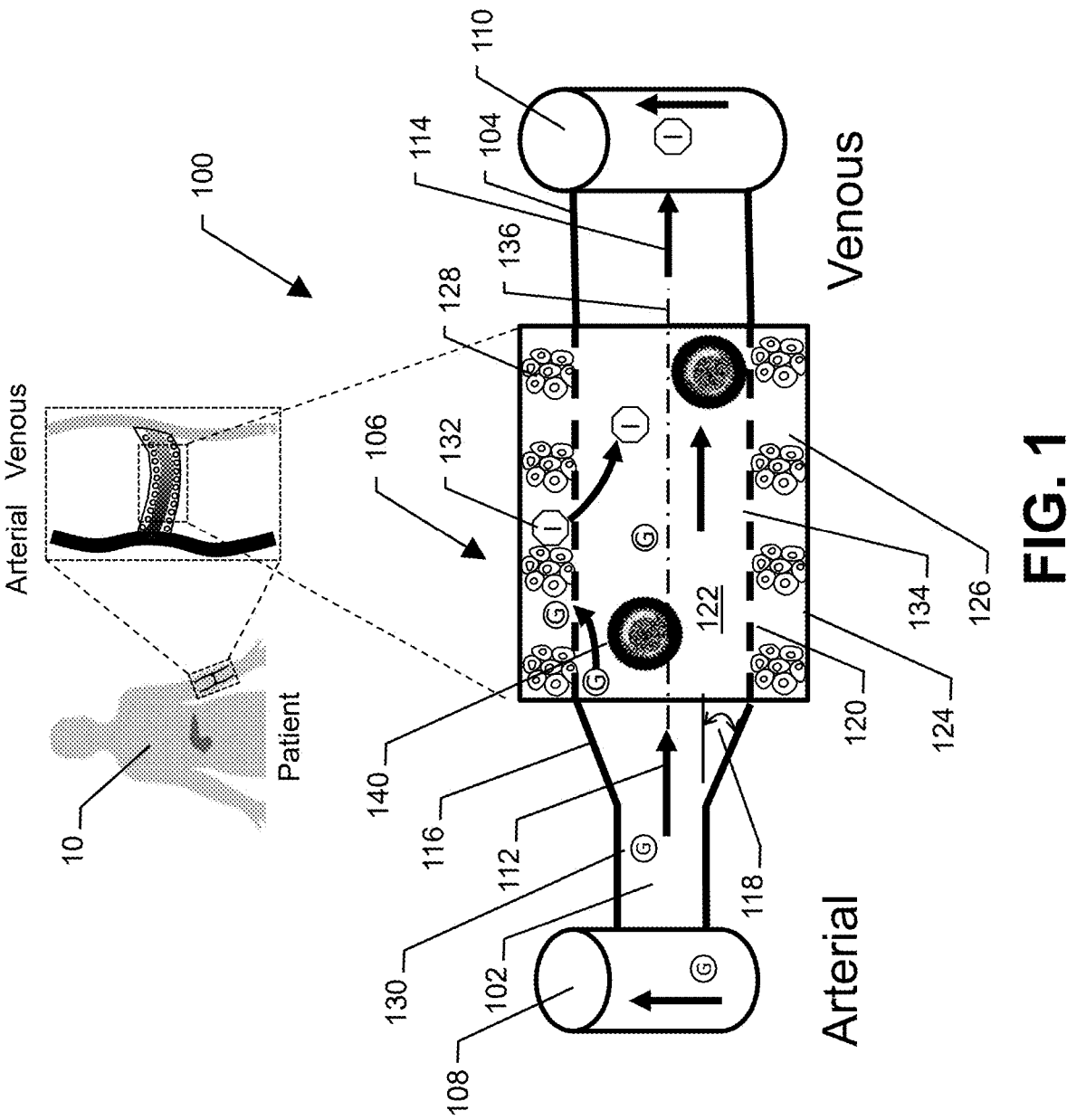
FIG. 1 is a schematic illustration of the transplantation graft in an arteriovenous configuration.

As illustrated in FIG. 1, the first end 102 of the transplantation graft 100 may be attached to an artery 108 and the second end 104 of the transplantation graft 100 may be attached to a vein 110 in an arteriovenous configuration. In this aspect, the first end 102, when attached to the artery 108, is configured to receive oxygenated arterial blood flow 112 and to direct the oxygenated arterial blood flow 112 into a lumen 122 within the treatment zone 106. The second end 104, when attached to the vein 110, is configured to direct blood flow 114 exiting the treatment zone 106 into the vein 110. Together, the first end 102, treatment zone 106, and second end 104 form a conduit to shunt a portion of oxygenated peripheral blood flow from the artery 108 to the vein 110 via the lumen 122 within the treatment zone 106. In various aspects, the first end 102 and the second end 104 may be attached to any suitable blood vessels of the peripheral circulatory system without limitation, so long as treatment zone 106 receives sufficiently oxygenated blood to maintain the activity of the plurality of transplanted cells, and the peripheral blood flow of the patient receives any biologically active compounds secreted or otherwise produced by the plurality of transplanted cells. By way of non-limiting example (not shown), the first end 102 and the second end 104 are both attached to the artery such that the first end 102 receives oxygenated arterial blood flow 112 and directs blood flow 114 exiting the treatment zone 106 back into the artery 108 downstream of the first end 102. In various other aspects, the graft 100 is attached in any configuration without limitation including, but not limited to, an arterial to venous configuration, an arterial to arterial configuration, or a venous to venous configuration.

Referring again to FIG. 1, in another aspect the transplantation graft 100 further includes a tubular tapered section 116 positioned between the first end 102 and the treatment zone 106. In this other aspect, the tapered section 116 is configured to expand and slow the flow speed of the arterial blood 112 entering the treatment zone 106. In various aspects, the taper angle 118 of the tapered section 116 is selected based on any one or more of a plurality of factors including, but not limited to: flow speed through the treatment zone 106 to enable sufficient oxygen exchange, carbon dioxide removal, and transport of other biologically active compounds to and from the transplanted cells within the treatment zone 106, and rate of removal of arterial flow from the artery 108 to limit the effect of shunting on tissue and organs positioned downstream from the transplantation graft 100.

In various aspects, the taper angle 118 of the tapered section 116 is modulated from about 10° to about 50° to hemodynamically modulate the amount of arterial blood flow entering into the graft. In various other aspects, the taper angle 118 is modulated from about 10° to about 14°, from about 12° to about 16°, from about 14° to about 18°, from about 16° to about 20°, from about 18° to about 22°, from about 20° to about 25°, from about 23° to about 28°, from about 25° to about 30°, from about 28° to about 33°, from about 30° to about 35°, from about 33° to about 38°, from about 35° to about 40°, from about 38° to about 43°, from about 40° to about 45°, from about 43° to about 48°, and from about 45° to about 50°.

In one aspect, the treatment zone 106 of the transplantation graft 100 includes a first graft layer 120 and a coating layer 124. Referring again to FIG. 1, the first graft layer 120 of the treatment zone 106 has a generally cylindrical or tubular shape defining a lumen 122 along a central longitudinal axis 136 of the treatment zone 106. The lumen 122 of the treatment zone 106 is configured to receive blood flow 112 as described above. Therefore, the cells 128 implanted in the treatment zone 106 have direct access to arterial blood flowing from the artery 108 at the first end 102 of the transplantation graft 100 to the vein 110 at the second end 104 of the transplantation graft 100. In various aspects, the treatment zone 106 ranges in diameter from about 4 mm to about 10 mm, from about 4 mm to about 6 mm, from about 5 mm to about 7 mm, from about 6 mm to about 8 mm, from about 7 mm to about 9 mm, and from about 8 mm to about 10 mm. In various other aspects, the length of the treatment zone 106 ranges from about 2 cm to about 40 cm, from about 2 cm to about 5 cm, from about 5 cm to about 10 cm, from about 7 cm to about 15 cm, from about 10 cm to about 20 cm, from about 15 cm to about 25 cm, from about 20 cm to about 30 cm, from about 25 cm to about 35 cm, and from about 30 cm to about 40 cm.

Figure 2:
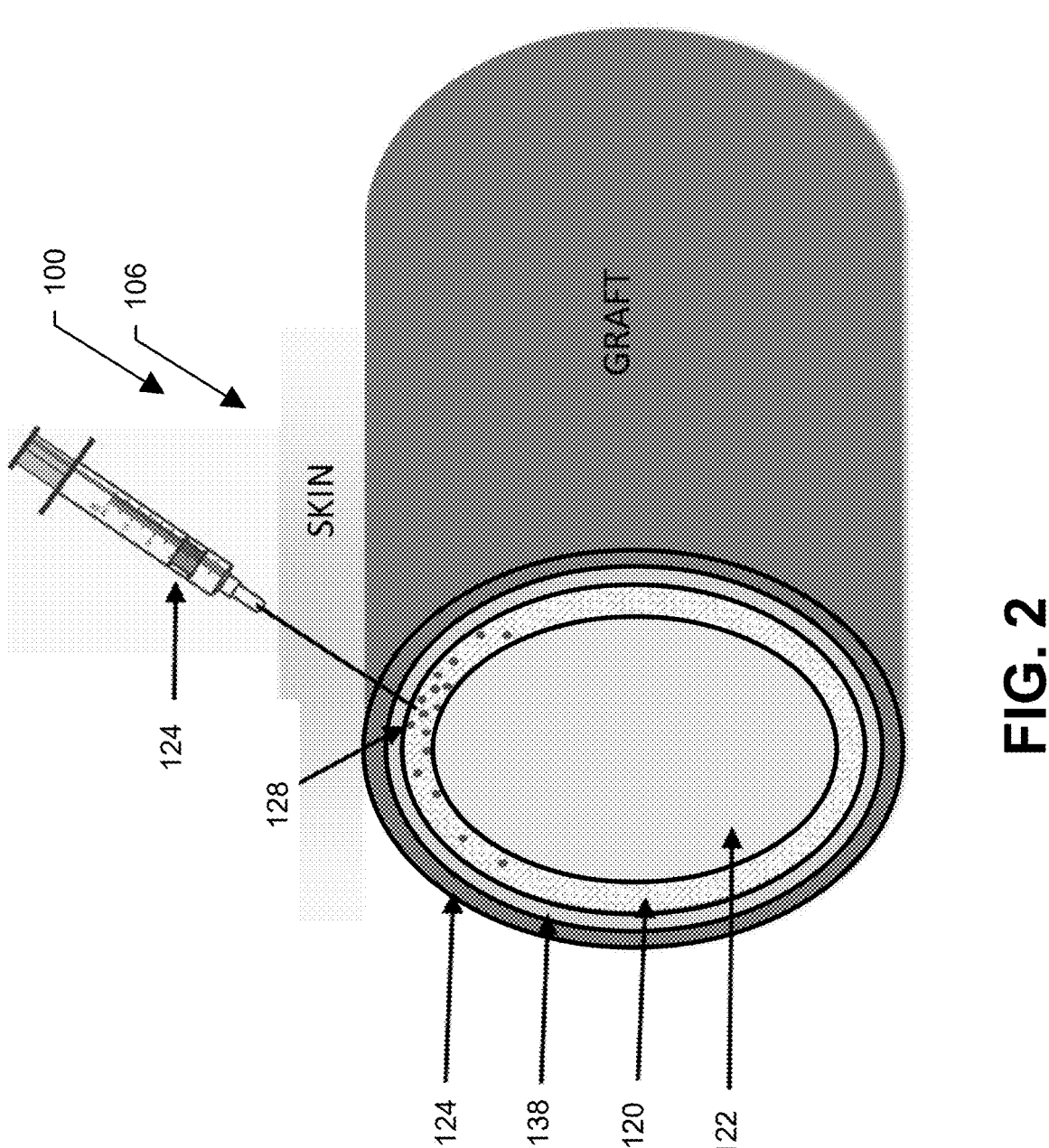
FIG. 2 illustrates one embodiment of the transplantation graft with a first PTFE graft layer with cells implanted within the layer, a second porous PTFE graft layer, and a hydrogel coating layer.

In various aspects, the treatment zone 106 of the transplantation graft 100 includes at least two layers. In some aspects, the treatment zone 106 includes two, three, or four layers. In one aspect, as illustrated in FIG. 2, treatment zone 106 of the transplantation graft 100 includes a first graft layer 120, a second graft layer 138, and a coating layer 124. The first graft layer 120 forms a lumen 122 and is in direct contact with the patient's blood once the graft 100 is implanted. The second graft layer 138 surrounds the first graft layer 120. The coating layer 124 surrounds the first graft layer 120 and the second graft layer 138. At least one of the first graft layer 120, second graft layer 138, or coating layer 124 includes a plurality of implanted cells 128 for transplantation into the patient 10 (see FIG. 1). In one aspect, the implanted cells 128 are imbedded within the first graft layer 120. In another aspect, the implanted cells 128 are imbedded within the second graft layer 138. In yet another aspect, the implanted cells 128 are imbedded within the coating layer 124. Any one of the first graft layer 120, second graft layer 138, and coating layer 124 may be degradable or non-degradable. Without being limited to any particular theory, the degradable layers 120/124/138 may promote neovascularization and release active compounds to both the patient 10 and the embedded cells 128.

In various aspects, the thickness of the coating layer 124 ranges from conformal up to about 1 mm. In various other aspects, the thickness of the coating layer 124 ranges from conformal up to about 0.2 mm, from about 0.1 to about 0.3 mm, from about 0.2 to about 0.4 mm, from about 0.3 to about 0.5 mm, from about 0.4 to about 0.6 mm, from about 0.5 to about 0.7 mm, from about 0.6 to about 0.8 mm, from about 0.7 to about 0.9 mm, and from about 0.8 to about 1 mm.

Referring again to FIG. 1, the first graft layer 120 in one aspect contains a plurality of pores 134 to enable any one or more of: implantation of the plurality of cells 128; diffusion of oxygen, nutrients and other biological factors 130 from the lumen 122 to the implanted cells 128; and the diffusion of carbon dioxide and biologically active agents 132 produced by the plurality of implanted cells 128 into the lumen 122. In one aspect, the first graft layer 120 includes a plurality of implanted cells 128, as illustrated in FIG. 2. In another aspect, the first graft layer 120 is void of cells at the time of implantation of the transplantation graft 100 into the patient 10. In various aspects, the lumen 122 defined within the first graft layer 120 contains a portion of the patient's blood.

In various aspects, the first graft layer 120 is reinforced to inhibit kinking or bending and thereby maintain patency of the treatment zone 106 of the transplantation graft 100 after implantation in the patient. Any reinforcement means known in the art may be used to reinforce the first graft layer 120 so long as the reinforcement does not interfere with the diffusion of oxygen, nutrients, biological factors 130, carbon dioxide, and biologically active agents across the first graft layer 120 as described above. Non-limiting examples of suitable reinforcement means include internal reinforcement such as a stent (not illustrated) positioned within the lumen 122 defined within the first graft layer 120, imbedded reinforcing elements such as stiffening fibers or strips embedded within the material forming the first graft layer 120, or external reinforcement such as a stent positioned between the outer surface of the first graft layer 120 and the second graft layer 138 and/or coating layer 124. By way of non-limiting example, an internal stent 146 provided to reinforce the first graft layer 120A is illustrated in FIG. 26. Additional description of the transplantation graft 100A illustrated in FIG. 26 is provided below.

Referring again to FIG. 2, the treatment zone 106 of the transplantation graft 100 includes a second graft layer 138 in some aspects. The second graft layer 138 surrounds the first graft layer 120. In various aspects, the second graft layer 138 may contain a plurality of implanted cells 128 or may be void of cells. In one aspect, the second graft layer contains a plurality of pores (not shown) similar to the plurality of pores 134 contained within the first graft layer 120 as described above. In various aspects, the plurality of pores within the first graft layer 120 and the second graft layer 138 each define a porosity of each layer. Without being limited to any particular theory, the porosity of each of the first graft layer 120 and the second graft layer 138 influence a plurality of different functions of the membranes including, but not limited to, the rate of diffusion of oxygen, nutrients and other biological factors 130 from the lumen 122 to the implanted cells 128; and the rate of diffusion of carbon dioxide and biologically active agents 132 produced by the plurality of implanted cells 128 into the lumen 122. In various aspects, the second graft layer 138 may have the same porosity as the first graft layer 120, or the second graft layer 138 may have a different porosity than the first graft layer 120. Non-limiting examples of materials that may be selected independently for use as the first graft layer 120 and/or second graft layer 138 include polytetrafluoroethylene (PTFE), expanded PTFE (ePTFE), stretch PTFE, polyethylene terephthalate (Dacron®), polyurethaneurea, polydimethylsiloxane (PDMS) and combinations thereof. In various aspects, pore sizes within the first graft layer 120 and the second graft layer 138 may range independently from about 1 nm to about 1000 nm, from about 1 nm to about 50 nm, from about 25 nm to about 100 nm, from about 50 nm to about 150 nm, from about 100 nm to about 300 nm, from about 200 nm to about 400 nm, from about 300 nm to about 500 nm, from about 400 nm to about 600 nm, from about 500 nm to about 700 nm, from about 600 nm to about 800 nm, from about 700 nm to about 900 nm, and from about 800 nm to about 1000 nm.

In various aspects, the coating layer 124 shields the implanted cells 128 from the patient's immune system, thereby inhibiting the rejection of the implanted cells 128 without the use of immunosuppressant drugs. The coating layer 124 is the outermost layer of the treatment zone 106 of the transplantation graft 100. In various aspects, the coating layer 124 surrounds the first graft layer 120 and/or the second graft layer 138, as illustrated in FIG. 1 and FIG. 2.

In one aspect, the coating layer 124 is formed from a hydrogel material. In various aspects, the hydrogel material may be porous or microporous. In various aspects, the coating layer 124 may include implanted cells 128 or may be void of cells. In some aspects, the coating layer 124 further includes biologically active agents for protecting the implanted cells 128 within the treatment zone 106 of the transplantation graft 100 from the patient's immune system. In some other aspects, the coating layer 124 provides a physical barrier between the implanted cells 128 and the patient's immune system. In one aspect, the coating layer is formed using a biocompatible hydrogel. Non-limiting examples of materials suitable for forming the coating layer 124 include alginate, triazole-thiomorpholine dioxide alginate, polyethylene glycol (PEG), PTFE, polyglycolic acid (PGA), poly-l-lactic acid (PLLA), polyhydroxyalkanoate, polycaprolactone-copolylactic acid, polylactide-coglycolide (PLGA), PDMS, polycaprolactone, and combinations thereof. In one aspect, the coating layer 124 may be formed using an alginate and PEG hydrogel.

In another aspect, the coating layer is formed using an impermeable membrane. FIG. 26 is a schematic illustration of a transplantation graft 100A that includes a treatment zone 106A that includes a first graft layer 120A enclosed by a coating layer 124A formed by an impermeable membrane enclosing the first graft layer 120A. In one aspect, the implanted cells 128 are positioned within a closed cavity 144 enclosed between the first graft layer 120A and the coating layer 124A. In various aspects, the implanted cells are introduced into the closed cavity 144 by injection through the impermeable membrane of the coating layer 124A. In various other aspects, the transplantation graft 100A is provided with an injection catheter (not illustrated) coupled to the coating layer 124A and forming a conduit into the closed cavity 144. One non-limiting example of an injection catheter is shown illustrated in FIG. 25.

In various aspects, the thickness of the closed cavity 144 (i.e. the separation of the coating layer 124A from the first graft layer 120A) ranges from about 1 mm to about 15 mm, from about 1 to about 3 mm, from about 2 to about 4 mm, from about 3 to about 5 mm, from about 4 to about 6 mm, from about 5 to about 7 mm, from about 6 to about 8 mm, from about 7 to about 9 mm, from about 8 to about 10 mm, from about 9 to about 11 mm, from about 10 to about 12 mm, from about 11 to about 13 mm, from about 12 to about 14 mm, and from about 13 to about 15 mm.

In various aspects, the cells 128 may be pre-loaded into the treatment zone 106 of the transplantation graft 100, loaded into the treatment zone 106 after implantation of the transplantation graft 100, and/or cells 128 may be periodically loaded into the treatment zone 106 of the transplantation graft 100 as needed. In one aspect, the treatment zone 106 of the transplantation graft 100 is seeded with cells prior to implantation in the patient 10. In another aspect, additional cells may be periodically injected using any suitable injection device 142 into the treatment zone 106 of the transplantation graft 100 as illustrated in FIG. 2 to replace cells that may have died or left the graft 100 after implantation. In various aspects, the transplanted cellular concentration and volume is variable depending on at least one factor of a plurality of factors including, but not limited to, the length of the treatment zone 106 of the transplantation graft 100 implanted in the patient 10, the desired amount of biological factors and/or biologically active agents 132 to be produced by the plurality of implanted cells 128, the predicted mortality of the plurality of implanted cells 128, and any other relevant factor.

In various aspects, the concentration of cells 128 to be transplanted using the transplantation graft 100 include any one or more of at least several factors including, but not limited to, the anticipated oxygenation needs of the cells 128, the volume within the patient 10 that the graft 100 can accommodate, the intended biological response needed from the cells 128. Without being limited to any particular theory, a minimum number off cells 128 to be transplanted is estimated in one aspect by evaluating the biological response for a particular transplanted cell type for the patient

10. In one aspect, a greater number of cells 128 are transplanted using the transplantation graft 100 is greater than the number needed to effectuate the desired biological response in anticipation of an initial decrease in cell population immediately after implantation. In some aspects, the population of cells is from about 10% to about 20% higher than needed, from about 10% to about 12%, from about 11% to about 13%, from about 12% to about 14%, from about 13% to about 15%, from about 14% to about 16%, from about 15% to about 17%, from about 16% to about 18%, from about 17% to about 19%, and from about 18% to about 20%.

Without being limited to any particular theory, the biological response effectuated by the graft 100 is modulated by the number of cells or other biological agents transplanted into the graft 100. In various aspects, the implanted cells are configure to contact any one or more biologically active agents 132 circulating in the arterial flow. Consequently, the plurality of cells 128 within the graft 100 are subject to patient-mediated modulation including, but not limited to negative or positive feedback biochemical pathways well known in the art with respect to physiological processes. Without being limited to any particular theory, a therapy administered using transplanted cells 128 with the transplantation graft 100 has the advantage of interacting with the patient's endogenous biochemical pathways via negative or positive feedback that is not typically achievable using conventional pharmacological interventions.

In some aspects, the transplantation graft 100 may be implanted using any suitable surgical technique known in the art including, but not limited to, the arteriovenous graft (AVG) implantation techniques used for hemodialysis access. In one aspect, the transplantation graft is surgically implanted in an arteriovenous configuration to the patient's peripheral arterial and venous systems. By way of non-limiting example, the transplantation graft 100 is connected to an artery 108 of the patient 10 at the first end 102 and to a vein 110 of the patient 10 at the second end 104. In some aspects, the transplantation graft 100 is implanted underneath the skin of the patient 10 and is accessible percutaneously. In other aspects, the transplantation graft 100 is implanted in an outpatient procedure.

Cell Transplantation

In various aspects, the first graft layer 120, the second graft layer 138, and/or the coating layer 124 are imbedded with cells 128 prior to implantation of the graft 100 or may be void of cells at prior to implantation. In some aspects, a plurality of implanted cells 128 are injected into the transplantation graft 100 after implantation, to seed the graft 100 and/or to replenish previously implanted cells.

In various aspects, the plurality of implanted cells 128 in the transplantation graft 100 are any cell type for which there is a need to transplant into the host patient. Non-limiting examples of patient needs that may influence the selection of cell types for implantation using the transplantation graft 100 as described herein include a patient need for an artificial organ, to replace a function in the body, or to replace dead or dysfunctional cells within the patient. Non-limiting examples of cell types suitable for implantation into a patient using the transplantation graft 100 include primary cells, pluripotent stem cells, differentiated stem cells, pancreatic cells, islet cells, β cells, cells specific to the thyroid, parathyroid, pituitary gland or adrenal gland, liver cells, genetically engineered cells, or any cell which secretes a biologically active agent. In various aspects, the implanted cells may be mammalian or human cells. In one aspect, the implanted cells are β cells derived from human pluripotent stem cells, also referred to herein as SC-β cells.

In various aspects, the transplantation graft provides the implanted cells with direct access to the patient's arterial blood, which provides rapid diffusion of oxygen, glucose, insulin, and other nutrients to the implanted cells 128. Without being limited to any particular theory, the oxygen content, which is essential for transplanted cell viability, in a peripherally implanted transplantation graft may be at least 2.5× higher than in microvascular tissue beds (see Example 1 below). Hypoxia after transplantation may cause necrosis in transplanted cells and even moderate hypoxia may greatly reduce the function of the transplanted cells. In various aspects, design features of the transplantation graft as described above reduce necrosis or moderate hypoxia in cells implanted in the transplantation graft by providing direct access to the patient's arterial blood.

In some aspects, the transplanted cells are selected to secrete a biologically active agent to a patient in need. In one aspect, the biologically active agent is secreted from the transplanted cells in response to stimulation by a biological factor present in the blood of the patient. Because of the direct access to the patient's arterial blood provided by the transplantation graft, the transplanted cells rapidly sense the concentration or presence of the biological factor in the patient's arterial blood. Without being limited to any particular theory, the close coupling of the implanted cells to the patient's arterial blood made possible by the transplantation graft provides for rapid sensing of biological factor in the patient's blood, as well as quick responses and feedback by the transplanted cells in response to changes in a biological factor in the blood. Non-limiting examples of biological factors in the patient's blood that may be sensed by the implanted cells within the transplantation graft include proteins, peptides, carbohydrates, polysaccharides, and any other suitable factor circulating within the patient's blood. In one aspect, the biological factor in the patient's blood is glucose or insulin.

In various aspects, the biologically active agent secreted from the implanted cells affects a physiological process or function in the body of the patient. In various other aspects, the transplanted cells absorb or consume a biological factor, thereby reducing the concentration and/or availability of the biological factor within the patient to affect physiological processes or functions in the body of the patient. In various aspects, the biologically active agent includes, but is not limited to, proteins, peptides, hormones, enzymes, proteases, or any other biologically active agent that may be secreted from the implanted cell. In one aspect, the biologically active agent is insulin. In other aspects, the biologically active agent is one of pancreatic hormones, thyroid hormones, parathyroid hormones, pituitary hormones, neuronal hormones, endocrine hormones, and other exocrine hormones. In additional aspects, the biologically active agent is one of growth factors, essential and nonessential enzymes, and biologically active synthetic proteins. In one aspect, the biological factor is glucose and the biologically active agent is insulin. In this example, transplanted β cells may sense the amount of glucose in the blood and secrete insulin at an appropriate rate in response to the amount of glucose detected. In an aspect, the insulin-secreting pancreatic β cells may be produced from stem cells.

By way of non-limiting example, a transplantation graft 100 includes a treatment zone 106 impregnated with insulin-producing pancreatic β cells 128 for the treatment of Type 1 diabetes, as illustrated in FIG. 1. In this example, the transplantation graft 100 including β cells 128 is configured to replace or reduce the need for a patient 10 to take insulin. Referring again to FIG. 1, the transplantation graft 100 receives glucose 130 circulating within the arterial blood of the patient 10 via the first end 102 attached to the patient's artery 108, which passes the arterial blood into the lumen 122 formed within the treatment zone 106 of the graft 100. The insulin-secreting pancreatic β cells 128 sense the concentration of glucose 130 rapidly diffused from the arterial blood within the lumen 122 through the pores 134 of the first graft layer 120. In response to the rapidly-detected glucose concentration, the β cells 128 secrete insulin 132, which rapidly diffuses out of the pores 134 of the first graft layer 120 into the lumen 122. The insulin 132 secreted into the lumen 122 is rapidly transferred back into the peripheral circulation of the patient 10 via the second end 104 attached to a vein 110 of the patient 10. In the arteriovenous transplantation grafts disclosed herein, the stem cell-derived β (SC-β) cells have direct access to the patient's oxygenated blood and nutrients in order to survive, have real-time sensing of arterial blood glucose fluctuations, and are able to rapidly deliver insulin into the venous circulation.

In one aspect, the cells impregnated within the treatment zone of the transplantation graft 100 are imbedded within alginate microbeads. The cells may be imbedded within the alginate microbeads using any method known in the art without limitation. By way of non-limiting example, FIG. 18 is a schematic illustration of a device 1800 for producing alginate beads with imbedded cells. Referring to FIG. 18, the device includes a feed tank 1802 containing a solution mixture 1804 including sodium alginate and the cells to be imbedded, a peristaltic pump 1806, an air compressor 1808, a spray nozzle 1810, and a polymerization tank containing a catalyst solution 1814. In use, the solution mixture 1804 is introduced into the spray nozzle via the peristaltic pump operatively coupled between the feed tank 1802 and the spray nozzle 1810. Driven by the air compressor 1808 coupled to the spray nozzle 1810, droplets 1816 of solution mixture 1804 formed by the spray nozzle are delivered to the polymerization tank 1812, which contains a catalyst solution including, but not limited to a solution containing $BaCl_2$. Upon contact with the catalyst solution 1814, the droplets 1816 harden into alginate beads with imbedded cells 1816. FIG. 19 shows a microscopic image of an alginate bead and FIG. 20 shows a microscopic image of an alginate bead with imbedded endothelial cells formed using droplets sprayed from a feed tank containing 390 microliters of 1.9% alginate: 145 microliter of cells/saline, with 7000 cells live cells.

By way of non-limiting example, alginate microbeads similar to those described above, but with imbedded SC-β cell clusters were formed using methods similar to those described above. FIG. 17A is a bright field microscopic image showing a SC-β cell cluster 1702 imbedded within an alginate bead 1704. Microbeads similar to those illustrated in FIG. 17A were implanted within diabetic mice, and the implanted mice were monitored for blood glucose and insulin concentrations, as compared to non-implanted healthy mice (control). FIG. 17B is a confocal immunofluorescence microscopic image of a microbead removed from a diabetic mouse 174 days after implantation; the bead was stained to indicate insulin production. FIG. 17C is a graph showing comparable blood glucose levels of the implanted diabetic and healthy control mice over the entire implantation period. FIG. 17D is a graph showing blood levels of Human C-peptide (a proxy for insulin production by the imbedded SC-β cell clusters in the implanted alginate beads); insulin production built up to stable levels about 100 days after implantation of the SC-β cell clusters in the diabetic mice.

In one aspect, the graft may be removed from the patient after a period of time, thus allowing complete retrieval of transplanted cells to ensure patient safety. In another aspect, the graft may be periodically replaced with a fresh graft. In an additional aspect, the graft remains in the patient after transplantation. In another additional aspect, additional cells are transplanted within the graft, which is not removed, to replenish the population of cells originally transplanted with the implantation of the graft.

Methods

Further provided herein is a method for transplanting cells into a patient. In one aspect, the method includes implanting a plurality of cells into a first graft layer or a coating layer of a transplantation graft and implanting the transplantation graft into the patient in an arteriovenous configuration. In another aspect, the cells may be implanted in the transplantation graft after the transplantation graft has been implanted in the patient.

Also provided herein is a method of treating a patient in need thereof. The method may include implanting a transplantation graft that includes plurality of implanted cells into the patient in an arteriovenous configuration, where the plurality of cells in the transplantation graft release a biologically active agent in response to a biological factor in blood flowing through the lumen of the transplantation graft. In one aspect, the transplantation graft implanted in the patient according to the disclosed method includes a first graft layer having a generally cylindrical configuration defining a lumen therethrough, a coating layer surrounding the first graft layer, and a plurality of cells. The implanted cells of transplantation graft implanted in the patient according to the disclosed method include, but are not limited to, pluripotent stem cells, differentiated stem cells, pancreatic cells, islet cells, β cells, thyroid cells, parathyroid cells, pituitary gland cells, and adrenal gland cells. In one aspect, the implanted cells are stem cell derived β cells. In various aspects, the implanted cells release a biologically active agent in response to a biological factor that includes, but is not limited to, proteins, peptides, carbohydrates, polysaccharides, and any other suitable biological factor within the blood of the patient. In one aspect, the biological factor is glucose. In various other aspects, the biologically active agent includes, but is not limited to, proteins, peptides, hormones, enzymes, and proteases. In one aspect, the biologically active agent is insulin. In one aspect, the patient in need thereof is a patient diagnosed with diabetes.

EXAMPLES

The following examples illustrate various aspects of the disclosure.

Example 1: Simulated Oxygen Profiles of Implanted Cells

To compare the oxygen profiles of cells implanted using the transplantation graft disclosed herein to cells transplanted using other existing methods, the following experiments were conducted. Finite element modeling was used to estimate the oxygen profile surrounding implanted cells within the transplantation graft compared to the corresponding oxygen profile surrounding implanted cells implanted within a microvasculature region. The finite element modeling simulated a 200 μm β cell cluster in a 600 μm thick hydrogel either surrounded on all sides by the microvasculature (40 mmHg) as illustrated in FIGS. 3A and 3B, or with one side beside arterial blood (95 mmHg), as illustrated in FIGS. 4A and 4B.

Figures 3A, 3B:
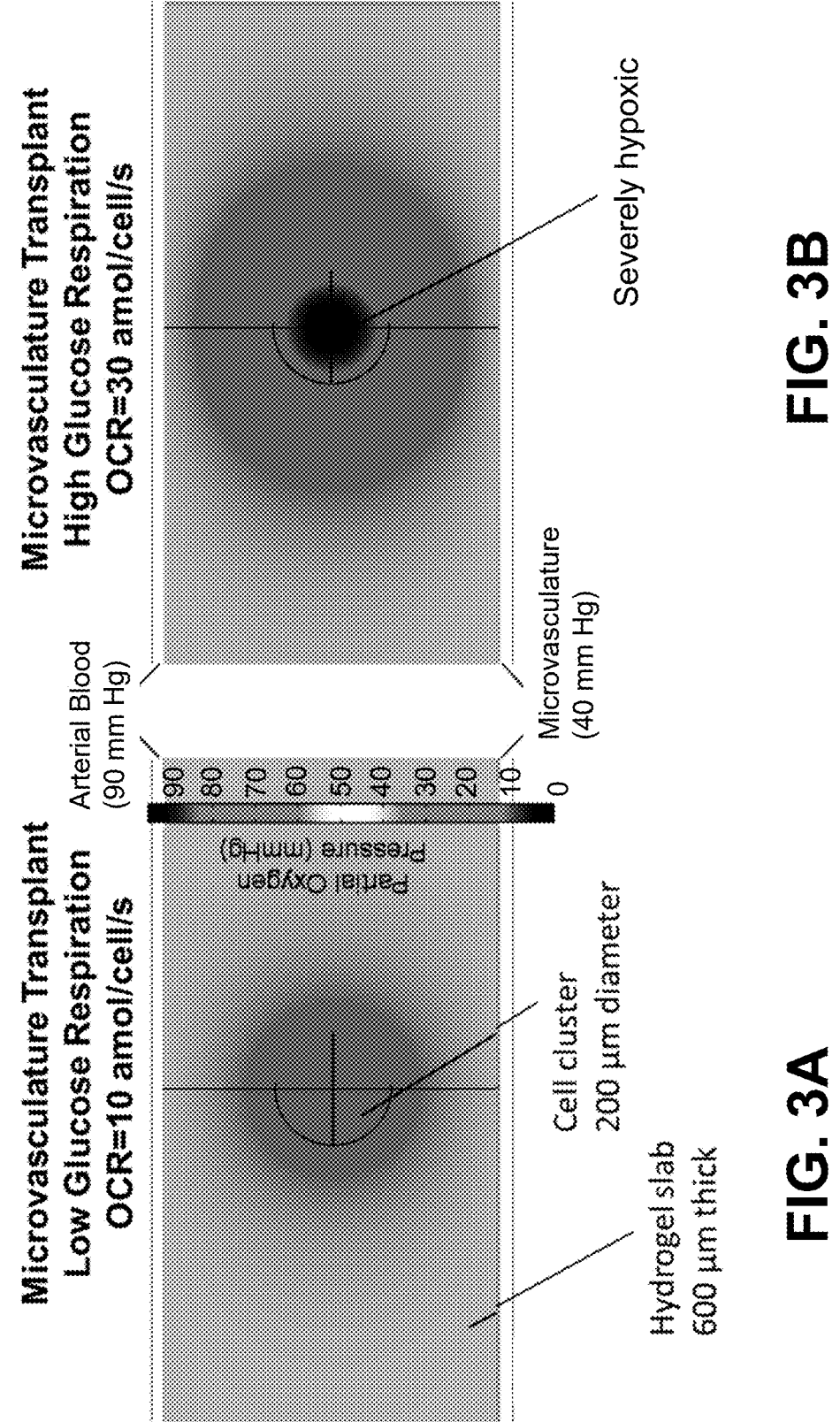
FIG. 3A is a map of oxygen concentration produced by a finite element model of a low glucose respiration cell cluster within a scaffold without access to arterial blood and low glucose respiration.
FIG. 3B is a map of oxygen concentration produced by a finite element model of a high glucose respiration cell cluster within a scaffold without access to arterial blood.
Figures 4A, 4B:
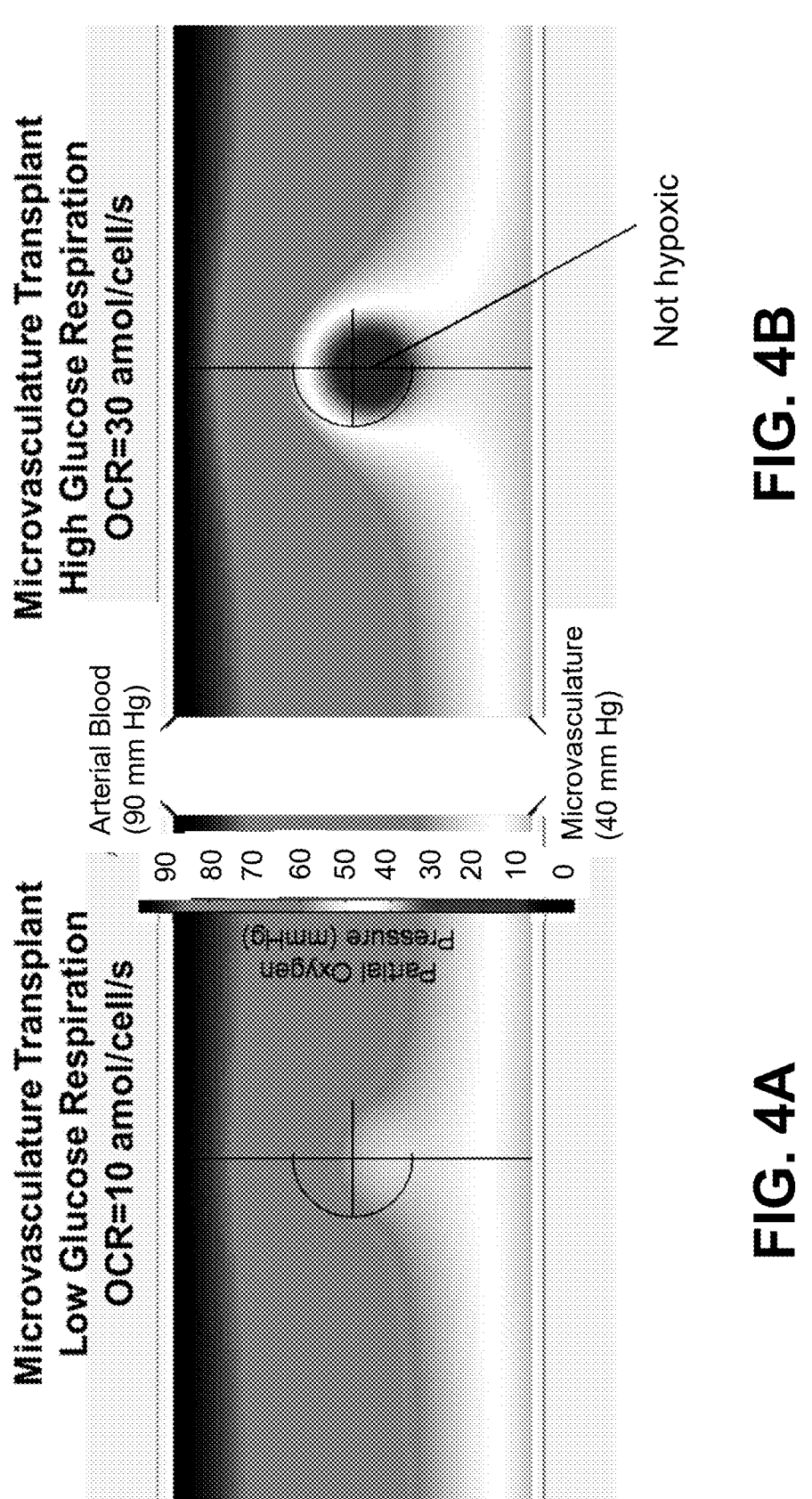
FIG. 4A is a map of oxygen concentration produced by a finite element model of a low glucose respiration cell cluster within a scaffold with access to arterial blood.
FIG. 4B is a map of oxygen concentration produced by a finite element model of a high glucose respiration cell cluster within a scaffold with access to arterial blood.
Figure 5:
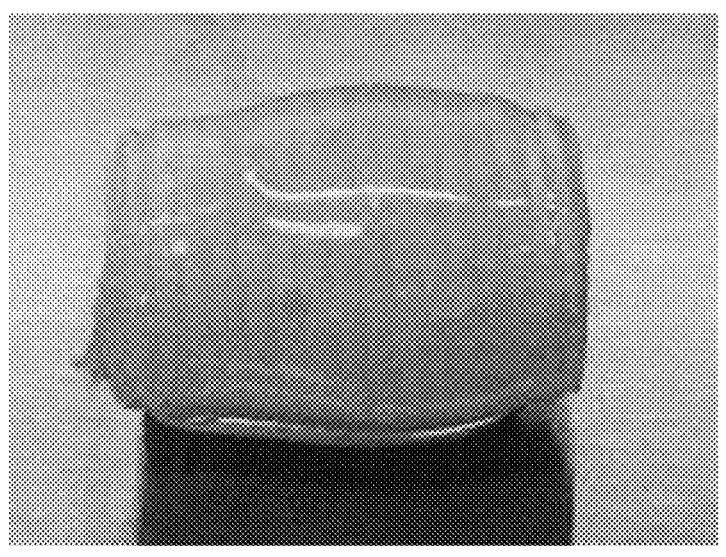
FIG. 5 is a photograph showing a side view of a transplantation graft in accordance with one aspect of the disclosure.
Figure 6:
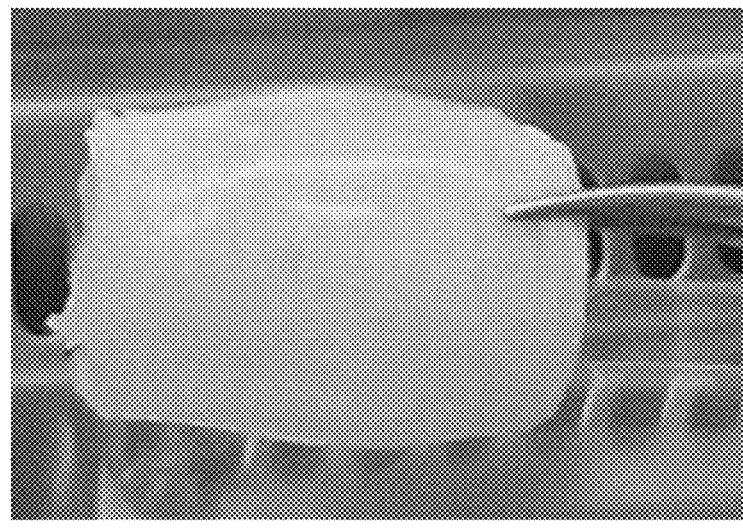
FIG. 6 is a photograph showing a close-up side view of the transplantation graft of FIG. 5.
Figure 7:
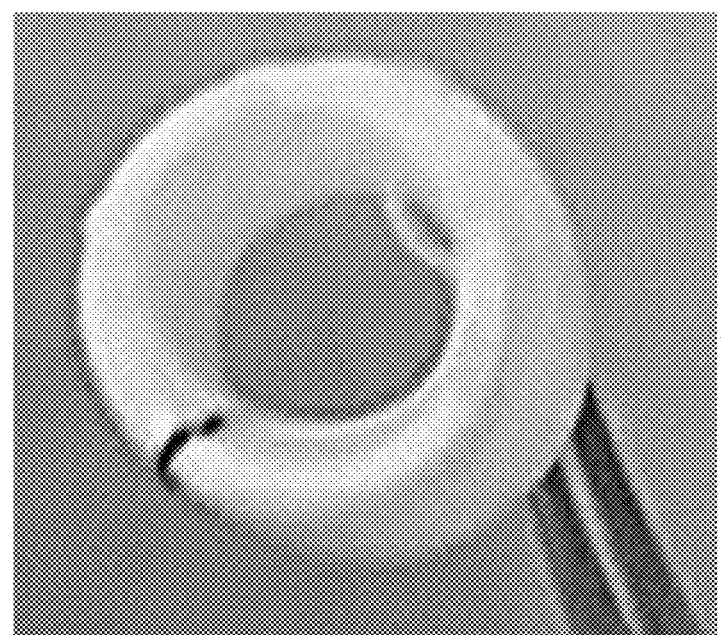
FIG. 7 is a photograph showing an end view of the transplantation graft of FIG. 5.
Figure 8:
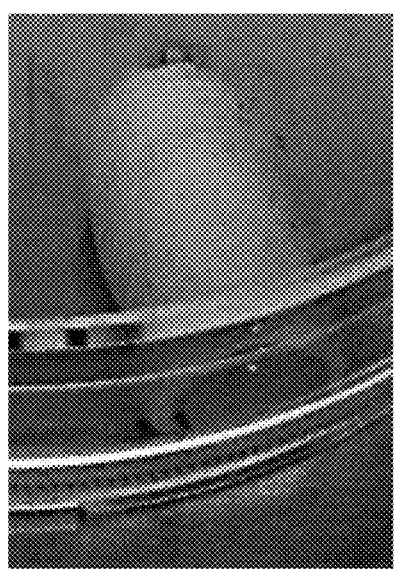
FIG. 8 is a photograph showing a top view of the transplantation graft of FIG. 5 with implanted cells.
Figure 9:
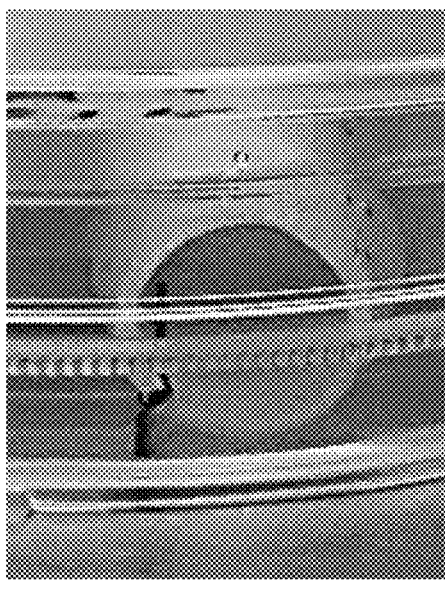
FIG. 9 is a photograph showing an end view of the transplantation graft of FIG. 8.

FIGS. 3A and 3B shows that oxygen delivery to encapsulated cells transplanted into the microvasculature was limited. FIG. 3A shows a microvasculature transplant with low glucose respiration and FIG. 3B shows a microvasculature transplant with high glucose respiration. FIGS. 4A and 4B shows that oxygen delivery to encapsulated cells transplanted proximal to arterial blood was enhanced relative to the oxygen delivery of microvasculature illustrated in FIGS. 3A and 3B. FIG. 4A shows a microvasculature transplant with low glucose respiration and FIG. 4B shows a microvasculature transplant with high glucose respiration.

The results of these experiments demonstrated increased oxygenation of tissue in the transplantation graft when the graft was adjacent to arterial blood on one side

Example 2: Fabrication of Transplantation Grafts

To demonstrate methods for fabricating the transplantation graft disclosed herein, the following experiments were conducted.

A major obstacle for developing cell replacement therapies for diabetes has been the lack of a renewable source of human pancreatic β cells. It has recently been shown that a large number of functional SC-β cells may be generated in vitro from human pluripotent stem cell (hPSC). Immature progenitor cells may be generated that can mature into β-like cells after several months in rodents. Indeed, current SC-β cells have many of the same features of bona fide β cells. However, transplantation of grafts that survive and function robustly remains a challenge.

Transplantation grafts were produced using an 8 mm Dacron vascular graft and an alginate hydrogel coating layer. The transplantation grafts were fabricated by dispersing cells within unpolymerized alginate, coating the outer portion of the vascular graft with the alginate/cell mixture, and dipping the coated vascular graft into a barium ion solution to induce polymerization of the alginate.

In a first transplantation graft, stem cell clusters were embedded in the alginate hydrogel. FIGS. 5, 6, 7, 8, and 9 are photographs of the transplantation graft produced using a PTFE and alginate with stem cell clusters. In a second transplantation graft, stem cell-derived β cell clusters were embedded in the hydrogel.

Figure 10A:
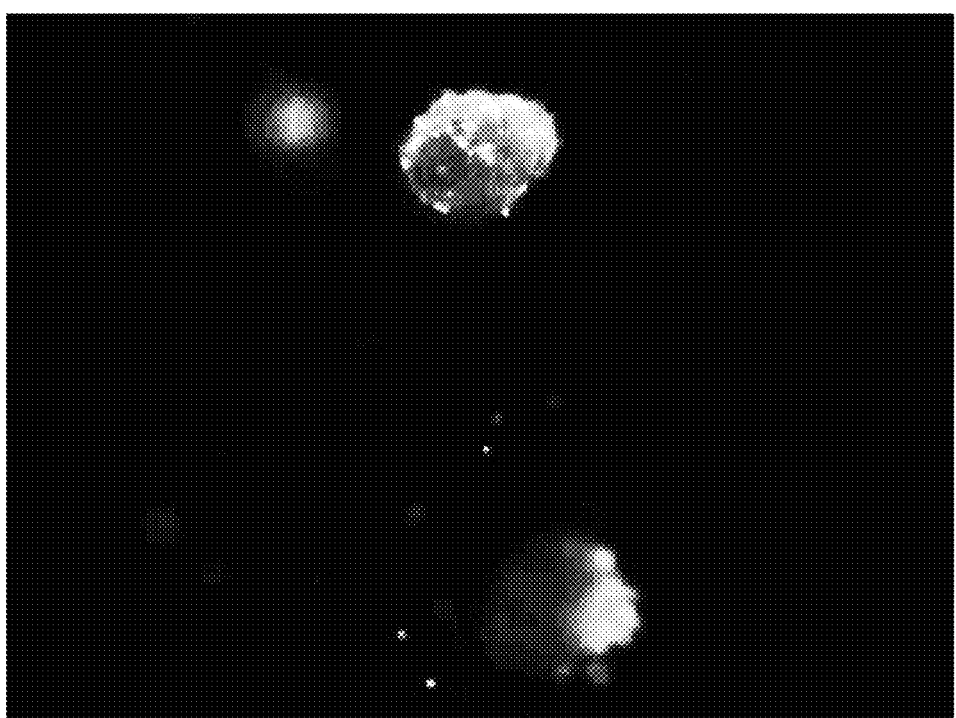
FIG. 10A is a microscopic image of transplanted cells within a transplantation graft in one embodiment, in which the cells are stained to identify dead cells.
Figure 10B:
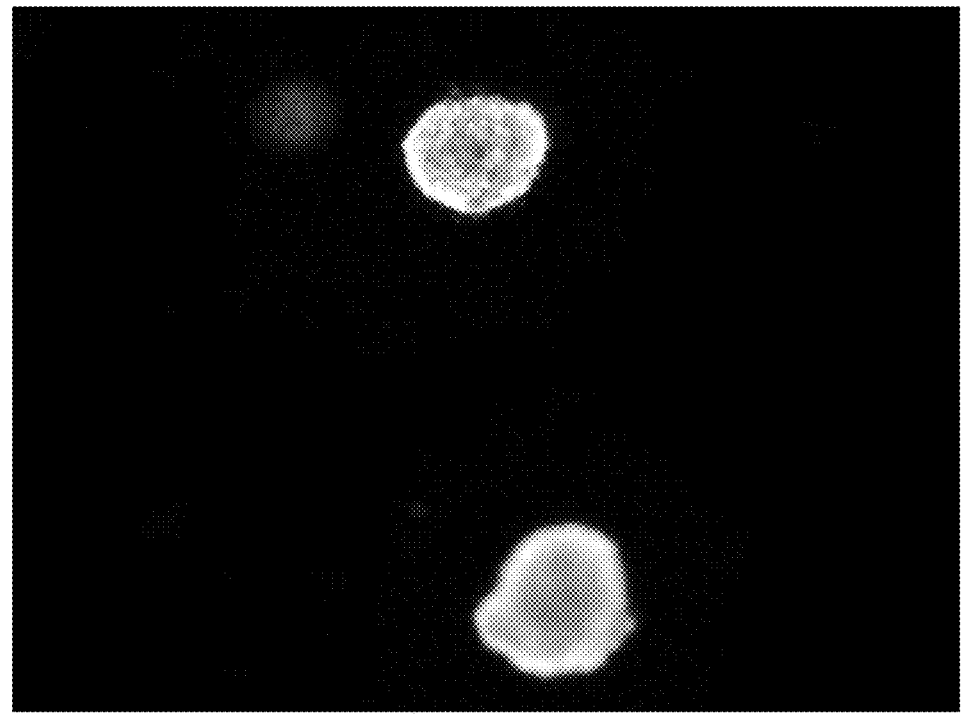
FIG. 10B is a microscopic image of transplanted cells within a transplantation graft in one embodiment, in which the cells are stained to identify living cells.
Figure 11A:
FIG. 11A is a microscopic image of transplanted cells within a transplantation graft in another embodiment, in which the cells are stained to identify dead cells.
Figure 11B:
FIG. 11B is a microscopic image of transplanted cells within a transplantation graft in another embodiment, in which the cells are stained to identify living cells.

The first and second transplantation grafts produced as described above were subjected to live/dead staining and inspected using microscopy to assess the condition of the implanted cells within the grafts. FIGS. 10A and 10B are microscopic images with live and dead staining, respectively, for the first transplantation graft. FIGS. 11A and 11B are microscopic images with live and dead staining, respectively, for the second transplantation graft. The microscopic images indicated that the cells implanted in both transplantation grafts displayed a high degree of viability.

Figure 12:
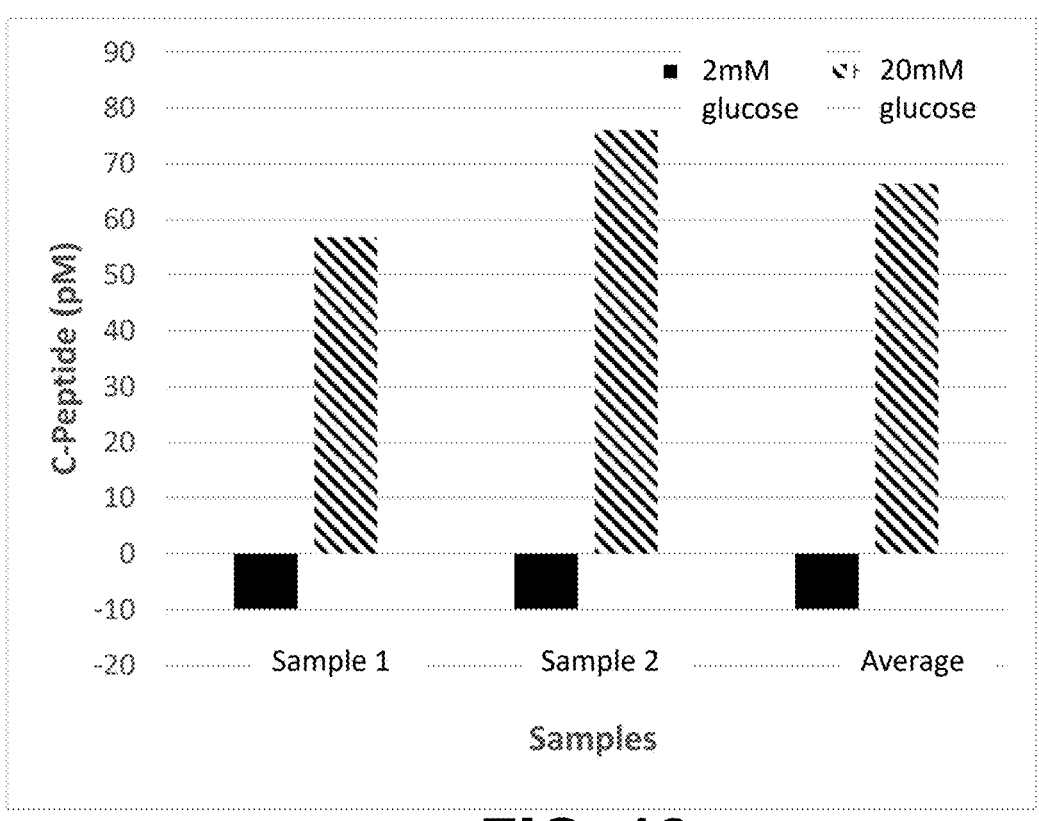
FIG. 12 is a graph summarizing the glucose-stimulated secretion of c-peptide (a proxy marker for insulin) by stem cell-derived β-cells embedded within a transplantation graft in one embodiment.
Figure 13:
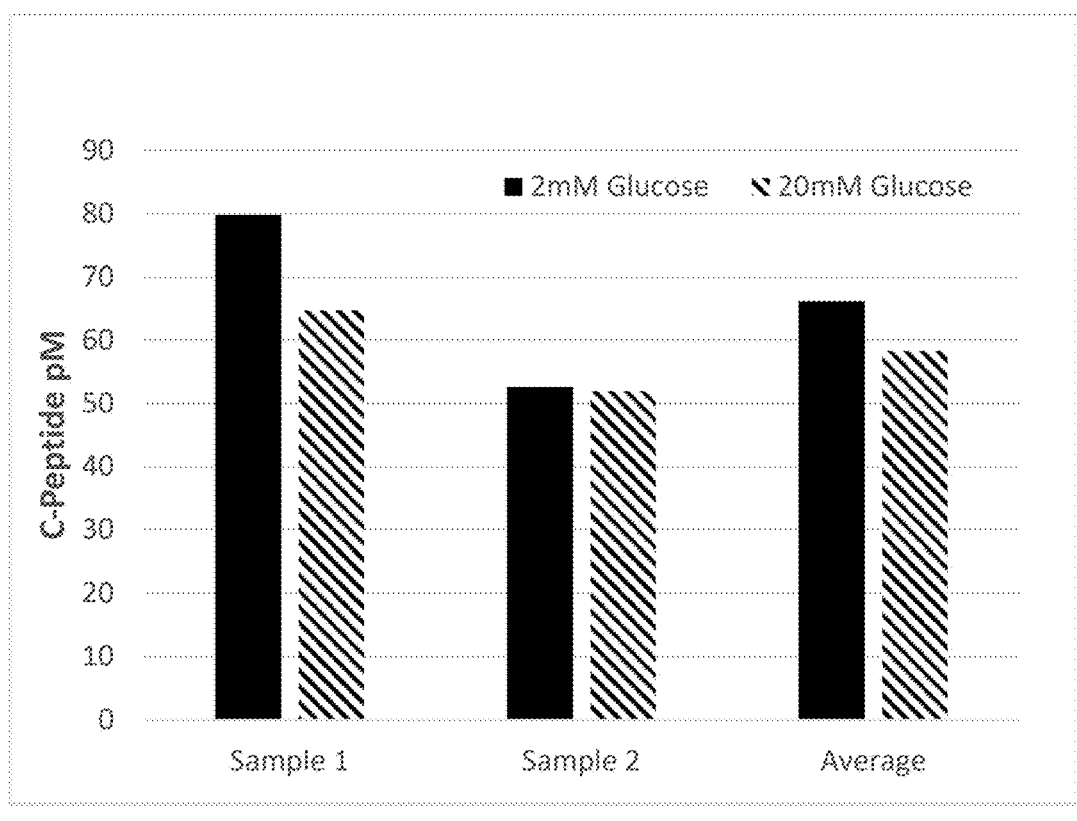
FIG. 13 is a graph summarizing the glucose-stimulated secretion of c-peptide (a proxy marker for insulin) by stem cell-derived β-cells embedded within a transplantation graft in another embodiment.

To assess the activity of the cells implanted in the first and second transplantation grafts, the grafts were cultured in solutions containing glucose at concentrations of 2 mM and 20 mM and concentrations of C-peptide produced by the cells (a proxy marker for insulin production) was measured. The measured C-peptide production of the first and second grafts are summarized in FIGS. 12 and 13, respectively. The results of this experiment demonstrated that the embedded SC-β cells in the first and second transplantation graphs secreted C-peptide in response to glucose.

Example 3: Effectiveness of Immune Cells Exclusion by Barrier Materials

To demonstrate the effectiveness of a candidate materials material for a transplantation graft at preventing the immunological attack of implanted cells, the following experiments were conducted.

SC-β cells and white blood cells were cultured in isolation, and combined. The combined SC-β cells and white blood cells were cultured without any physical barrier, separated by a 0.4 micron PET membrane, and separated by the PET membrane as well as an additional hydrogel barrier. The cell cultures were subjected to microscopic imaging as well as to confocal imaging with red staining to identify C-peptide fragments associated with insulin production by the SC-β cells.

Figure 14:
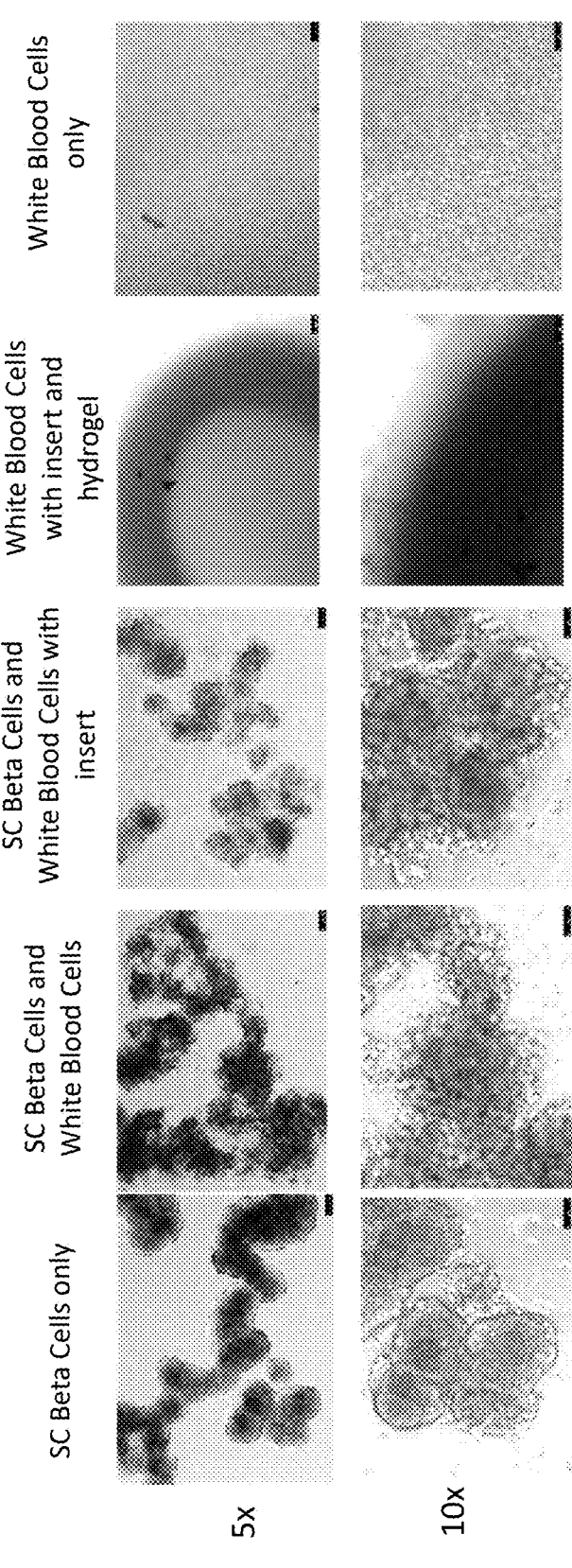
FIG. 14 contains a series of microscopic images of stem cell-derived β-cells and white blood cells in isolation, separated by a 0.4 μm PET membrane, and separated by the 0.4 μm PET membrane with a hydrogel outer layer.
Figure 15:
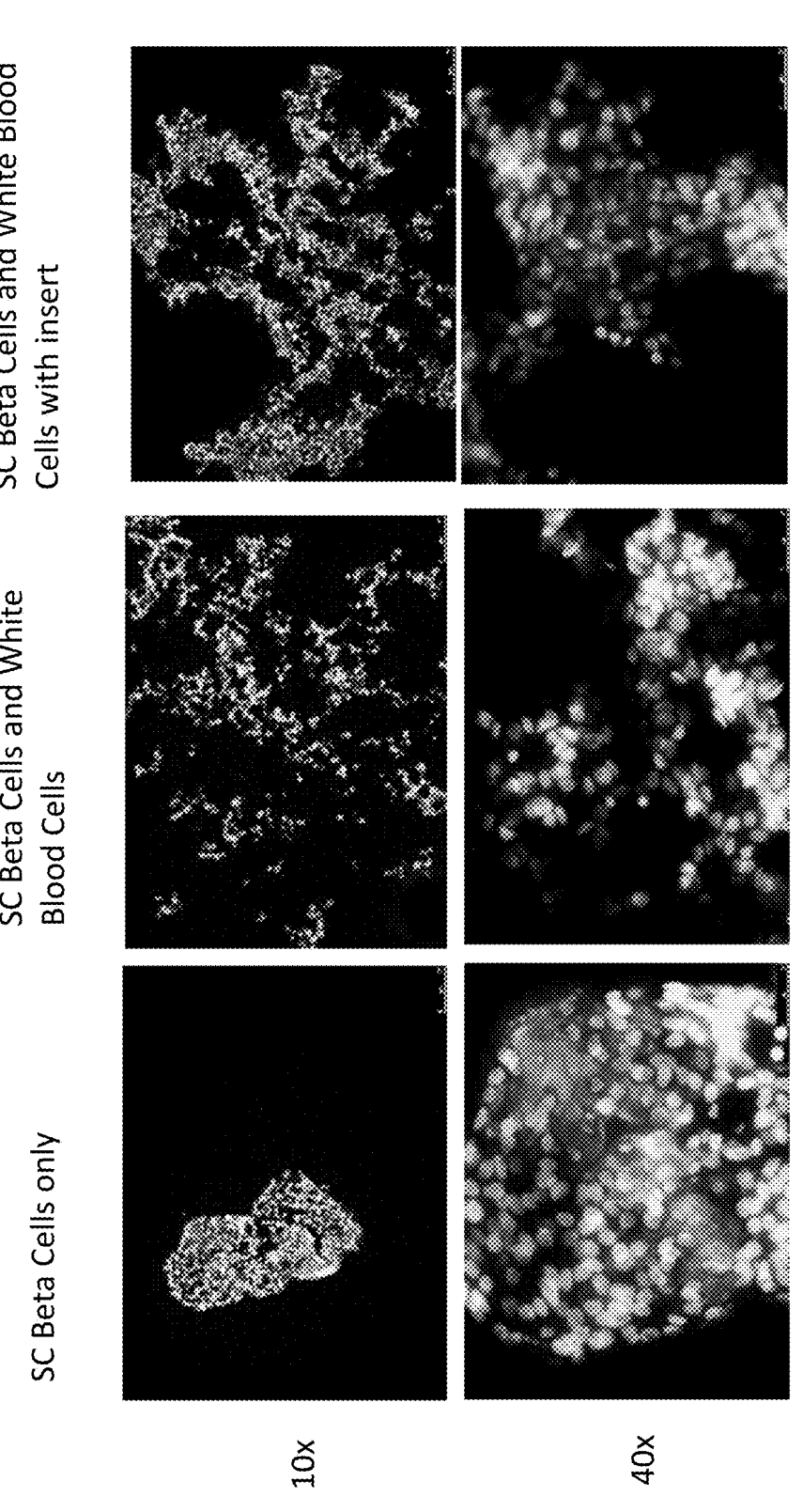
FIG. 15 contains a series of microscopic images of stem cell-derived β-cells and white blood cells in isolation, separated by a 0.4 μm PET membrane, and separated by the 0.4

FIG. 14 contains a series of microscopic images of the different cultures at magnifications of 5× (top row) and 10× (bottom row) for the different combinations of SC-β cells, white blood cells, and barriers. FIG. 15 contains a series of confocal microscopy images stained to detect C-peptide for the SC-β cells in isolation, SC-β cells and white blood cells with no barrier, and SC-β cells and white blood cells separated by the 0.4 micron PET membrane. As indicated by FIGS. 14 and 15, the 0.4 micron PET membrane provided immune protection for the SC-β cells, and retained cell function, as indicated by the insulin production demonstrated by the detection of C-peptide fragment with red stain in FIG. 15.

Example 4: Hydrogel Encapsulation of Cells

To assess a method of encapsulating cells within a hydrogel polymer, the following experiments were conducted.

SC-β cells were mixed with various liquid hydrogel solutions, followed by polymerization of the hydrogel at different conditions. The cells were mixed with polymer solutions having a volumes of 1 mL at 4° C. and then cured at 37° C. overnight. FIG. 16 contains a series of photographs of the cell/polymer mixtures immediately after mixing, after curing for 10 min, after curing for about 1 hour, and after curing overnight. As illustrated in the images of FIG. 16, the hydrogel cured relatively slowly, causing the cells to settle to the bottom of the mixture, rather than be suspended within the hydrogel.

The results of this experiment demonstrated the sensitivity of encapsulation of transplant cells to the setting time of the encapsulating hydrogel. In some aspects, the polymerization time is selected to provide sufficient time to distribute the implanted cells throughout the hydrogel volume while simultaneously setting quickly enough to maintain the suspended distribution of the cells within the cured hydrogel.

Example 5: Encapsulation of SC-β Cells in Alginate Beads

To validate the use of the method of encapsulating cells within alginate beads as disclosed above, the following experiments were conducted.

Stem cell-derived β (SC-β) cells were encapsulated within alginate beads using the methods similar to those described above. The alginate beads were stained with a first stain to demarcate living SC-β cells and with a second stain to demarcate dead SC-β cells. The stained alginate beads loaded with SC-β cells were subjected to confocal immunofluorescent microscopy to assess the relative abundance of living versus dead SC-β cells.

FIG. 21A is a confocal microscopic image of a single alginate bead showing the SC-β cells distributed throughout the bead volume. FIG. 21B is a confocal immunofluorescent microscopic image showing the stained live SC-β cells, and FIG. 21C is a confocal immunofluorescent microscopic image showing the stained dead SC-β cells. Comparing FIGS. 21B and 21C, the confocal immunofluorescent microscopic images confirmed cell embedding within the alginate microbeads and that a significant proportion of the cells were alive.

Example 6: Diffusion of Glucose and Insulin Through Porous Membrane Materials To compare the diffusion rates of glucose and insulin through several different porous membrane materials, the following experiments were conducted.

Three different membrane materials were mounted in diffusion cells: porous polyethylene terephthalate (PET) with porosities ranging from about 0.1 to about 1.0 (see FIG. 22A), electrically spun PET formed from 135-micron fibers (FIG. 23A), and electrically spun (polyacrylonitrile) PAN (FIG. 24A). The diffusion of glucose and of insulin was assessed within the diffusion cells mounted with the different membrane compositions.

FIGS. 22B, 23B, and 24B summarize the diffusion of glucose across the porous PET, electrically spun PET, and electrically spun PAN, respectively. FIGS. 22C, 23C, and 24C summarize the diffusion of insulin across the porous PET, electrically spun PET, and electrically spun PAN, respectively.

The results of these experiments demonstrated that glucose and insulin diffused through all membrane compositions, that glucose diffused more readily through the PET membrane compositions, and that insulin diffused more readily through the PAN membrane compositions.

Example 7: Implantation of Transplantation Graft in Porcine Subject

To validate the surgical methods for implanting a transplantation graft similar to those described above and the function of the implanted graft, the following experiments were conducted.

FIG. 25 is a photograph of the transplantation graft assembled for transplantation in a pig. This transplantation graft included a treatment zone that included a microporous tubular membrane sealed within a surrounding impermeable membrane. The microporous tubular membrane was internally reinforced with a stent (not shown) to resist kinking and bending while still allowing flow through the microporous treatment membrane. Each end of the treatment zone was spliced to a section of vascular graft tubing and an injection catheter was attached such that the distal end of the catheter opened into the volume enclosed between the outer impermeable membrane and the inner microporous membrane of the treatment zone. The transplantation graft illustrated in FIG. 25 was attached between the internal carotid artery and the external jugular vein of four pigs as summarized in the series of images of FIG. 27. Alginate microbeads similar to the microbeads described in Example 5 were injected into the treatment zone via the injection catheter. Pulsatile flow was directly observed though the treatment zone prior to closing up the incision used to access the implantation region of the pig.

The neck region of the pig with the implanted graft is shown in FIG. 28. After closing the incision, the pig was subjected to ultrasound imaging with Doppler to confirm graft position and patency. FIG. 29 is an ultrasound image showing the region indicated by a dashed rectangle super-imposed on FIG. 28, demonstrating the correct positioning of the graft after closing. FIG. 30 is a Doppler ultrasound image showing the region indicated by a solid rectangle superimposed on FIG. 28, demonstrating pulsatile flow within the treatment zone of the graft after closing. FIG. 31 is a Doppler ultrasound analysis of the flow rate through a portion of the treatment zone shown in FIG. 30, confirming arteriovenous flow through the treatment zone of the graft. In two pigs the graft stayed patent for roughly two weeks, and in the remaining two pigs the graft remained patent for 24 days after implantation.

Three or four weeks after implantation of the graft shown in FIG. 25, the pigs were sacrificed and the grafts were removed and dissected to assess the grafts for defects and patency of the treatment zone of each graft. FIG. 32 is an image of one dissected graft, showing no obstructions or defects within the treatment zone after 3-4 weeks implanted in the pig. Note that the stent used to internally reinforce the inner microporous membrane of the treatment zone is visible in this image.

The results of these experiments validated the surgical method for implanting the transplantation grafts, the estab-lishment of pulsatile blood flow through the implanted grafts, and the maintenance of patency of the implanted grafts over extended implantation periods.

Having described several embodiments, it will be recog-nized by those skilled in the art that various modifications, alternative constructions, and equivalents may be used with-out departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A transplantation graft for transplanting cells into a patient, the graft comprising:
 a first graft layer having a generally cylindrical configu-ration and defining a lumen configured to receive a blood flow of the patient directly therethrough, wherein the first graft layer directly contacts the blood flow within the lumen;
 a non-alginate coating layer surrounding the first graft layer; and
 a plurality of implanted cells encapsulated within a plu-rality of alginate microbeads imbedded within either the first graft layer or the non-alginate coating layer,
 wherein the transplantation graft is configured to be implanted in the patient in an arteriovenous configu-ration, and
 wherein the non-alginate coating layer protects the implanted cells from the patient's immune system.

2. The transplantation graft of claim 1, wherein the plurality of cells in the transplantation graft release a bio-logically active agent in response to a biological factor in blood flowing through the lumen of the transplantation graft.

3. The transplantation graft of claim 1 further comprising a non-alginate second graft layer between the first graft layer and the non-alginate coating layer.

4. The transplantation graft of claim 3, wherein the first graft layer, the non-alginate second graft layer, and any combination thereof is porous or microporous.

5. The transplantation device of claim 3, wherein the second graft layer comprises polytetrafluoroethylene (PTFE), expanded PTFE (ePTFE), stretch PTFE, polyeth-ylene terephthalate, polyurethaneurea, polydimethylsi-loxane (PDMS), or combinations thereof.

6. The transplantation graft of claim 1, wherein the implanted cells are within the first graft layer.

7. The transplantation graft of claim 1, wherein the implanted cells are within the non-alginate coating layer.

8. The transplantation device of claim 1, wherein the first graft layer comprises polytetrafluoroethylene (PTFE), expanded PTFE (ePTFE), stretch PTFE, polyethylene tere-phthalate, polyurethaneurea, polydimethylsiloxane (PDMS), or combinations thereof.

9. The transplantation device of claim 1, wherein the non-alginate coating layer comprises, polyethylene glycol (PEG), PTFE, polyglycolic acid (PGA), poly-l-lactic acid (PLLA), polyhydroxyalkanoate, polycaprolactone-copoly-lactic acid, polylactide-coglycolide (PLGA), PDMS, poly-caprolactone, or combinations thereof.

10. The transplantation device of claim 9, wherein the coating layer consists of PEG.

11. The transplantation device of claim 1, wherein the implanted cells are selected from the group consisting of primary cells, pluripotent stem cells, differentiated stem cells, pancreatic cells, islet cells, β cells, thyroid cells, parathyroid cells, pituitary gland cells, adrenal gland cells, liver cells, genetically engineered cells, and any cell which secretes a biologically active agent.

12. A method for transplanting cells into a patient com-prising:
 providing a transplantation graft comprising:
  a first graft layer having a generally cylindrical con-figuration and defining a lumen configured to receive a blood flow of the patient directly therethrough, wherein the first graft layer directly contacts the blood flow within the lumen;
  a non-alginate coating layer surrounding the first graft layer; and
  a plurality of implanted cells encapsulated within a plurality of alginate microbeads imbedded within either the first graft layer or the non-alginate coating layer, wherein the transplantation graft is implanted in the patient in an arteriovenous configuration, and the non-alginate coating layer protects the implanted cells from the patient's immune system;
 implanting the plurality of cells into the first graft layer or the non-alginate coating layer of the transplantation graft; and
 implanting the transplantation graft into the patient in an arteriovenous configuration.

13. The method of claim 12, wherein the plurality of implanted cells are implanted in the transplantation graft after the transplantation graft has been implanted in the patient.

14. A method of treating a patient in need thereof, comprising, implanting a transplantation graft comprising:

a first graft layer having a generally cylindrical configuration and defining a lumen configured to receive a blood flow of the patient therethrough, wherein the first graft layer directly contacts the blood flow within the lumen;

a non-alginate coating layer surrounding the first graft layer; and a plurality of implanted cells encapsulated within a plurality of alginate microbeads imbedded within either the first graft layer or the non-alginate coating layer, into the patient in an arteriovenous configuration, wherein the non-alginate coating layer protects the implanted cells from the patient's immune system;

wherein the plurality of implanted cells in the transplantation graft release a biologically active agent in response to a biological factor in blood flowing through the lumen of the transplantation graft.

15. The method of claim 14, wherein the implanted cells are selected from the group consisting of primary cells, pluripotent stem cells, differentiated stem cells, pancreatic cells, islet cells, β cells, thyroid cells, parathyroid cells, pituitary gland cells, adrenal gland cells, liver cells, genetically engineered cells, and any cell which secretes a biologically active agent.

16. The method of claim 14, wherein the implanted cells are stem cell derived β cells.

17. The method of claim 14, wherein the biological factor is selected from the group consisting of proteins, peptides, carbohydrates, polysaccharides, and any factor within the blood.

18. The method of claim 17, wherein the biological factor is glucose.

19. The method of claim 14, wherein the biologically active agent is selected from the group consisting of proteins, peptides, hormones, enzymes, and proteases.

20. The method of claim 19, wherein the biologically active agent is insulin.

* * * * *